US006458026B1

(12) United States Patent
Hart

(10) Patent No.: US 6,458,026 B1
(45) Date of Patent: Oct. 1, 2002

(54) INTEGRIN-TARGETING VECTORS HAVING TRANSFECTION ACTIVITY

(75) Inventor: Stephen L. Hart, London (GB)

(73) Assignee: ICH Productions Limited, London (GB)

( * ) Notice: Subject to any disclaimer, the term of this patent is extended or adjusted under 35 U.S.C. 154(b) by 0 days.

(21) Appl. No.: 09/424,656

(22) PCT Filed: May 29, 1998

(86) PCT No.: PCT/GB98/01577

§ 371 (c)(1),
(2), (4) Date: Nov. 29, 1999

(87) PCT Pub. No.: WO98/54347

PCT Pub. Date: Dec. 3, 1998

(30) Foreign Application Priority Data

May 29, 1997 (GB) .............................................. 9711115

(51) Int. Cl.[7] .......................... C12N 15/63; C12N 15/88
(52) U.S. Cl. ...................... 453/69.1; 435/455; 435/458; 435/320.1; 435/325; 424/450
(58) Field of Search ...................... 514/44, 2; 424/450; 435/320.1, 455, 69.1; 536/23.1, 24.5; 530/300, 326

(56) References Cited

FOREIGN PATENT DOCUMENTS

| WO | WO 95/14714 | * | 6/1995 |
|----|-------------|---|--------|
| WO | WO 9514714 A |  | 6/1995 |
| WO | WO 96/15811 | * | 5/1996 |
| WO | WO 96 15811 A |  | 5/1996 |
| WO | WO 96/40961 | * | 12/1996 |
| WO | WO 96 40961 A |  | 12/1996 |
| WO | WO 97 00965 A |  | 1/1997 |

OTHER PUBLICATIONS

Anderson et al., "Human gene therapy", Nature, 392 (Supp.):25–30, Apr. 1998.*
Verma and Somia, "Gene therapy–promises, problems and prospects", Nature, 389:239–242, Sep. 1997.*
Valsesia–Wittmann et al., "Modifications in the binding domain of avian retrovirus envelope protein to redirect the host range of retroviral vectors", J. Virol., 68(7):4609–4619, Jul. 1994.*
Genbank Accession No., S35430, accessed by PTO, Apr. 10, 2000, May 1999.*
Kaplan et al., "Potentiation of Gene Transfer to the Mouse Lung by Complexes of Adenovirus Vector and Polycations Improves Therapeutic Potential", Human Gene Therapy, 9: 1469–1479, (Jul. 1, 1998).
Hart et al., "Cell Binding and Internalization by Filamentous Phage Displaying a Cyclic Arg–Gly–Asp-containing Peptide", The Journal of Biological Chemistry, vol. 269, No. 17, Apr. 29, 1994, pp. 12468–12474.

Hart et al., "Gene Delivery and Expression Mediated by an Integrin–Binding Peptide", Gene Therapy (1995), 2, pp. 552–554.
Hart et al., "Integrin–Mediated Transfection with Peptides Containing Arginine–Glycine–Aspartic Acid Domains", Gene Therapy (1997) 4, pp. 1225–1230.
Shewring et al., "A Nonviral Vector system for Efficient Gene Transfer to Corneal Endothelial Cells Via Membrane Integrins", Transplantation, vol. 64, 763–769, No. 5, Sep. 15, 1997.
Farhood et al., "The role of dioleoyl phosphatidylethanolamine in cationic liposome mediated gene transfer", Medline Express (R) 1994–1996, Biochim–Biophys–Acta. May 4, 1995; 1235(2): 289–95.
Zhou–X, "DNA transfection mediated by cationin liposomes containing lipopolylysine: characterization and mechanism of action", Medline Express (R) 1994–1996, Biochim–Biophys–Acta. Jan. 19, 1994; 1189(2): 195–203.
Bailey et al., "pH–induced destabilization of lipid bilayers by a lipopeptide derived from influenza hemagglutinin", Medline Express (R) 1997–1999, Biochim–Biophys–Acta. Mar. 13, 1997; 1324(2): 232–44.
Ramy et al., "Targeted gene transfer into hepatoma cells with liopolyamine–condensed DNA particles presenting glactose ligands: a stage toward artificial viruses", Medline Express (R) 1994–1996, Proc–Natl–Acad–Sci–USA, Feb. 28, 1995; 92(5): 1744–8.
Schutzbach et al., "Bilayer membrane destabilization induced by dolichylphosphate", Medline Express (R) 1986–1990, Chem–Phys–Lipids. Nov. 1989; 51(3–4): 213–8.
Kikuchi et al., "Efficient gene transfer to EGF receptor overexpressing cancer cells by means of EGF–labeled cationic liposomes", Medline Express (R) 1994–1996, Biochem–Biophys–Res–Commun., Oct. 23, 1996; 227(3): 666–71.
Lewis et al., "A serum–resistant cytofectin for cellular delivery of antisense oligodeoxynucleotides and plasmid DNA", Medline Express (R) 1994–1996, Prox–Natl–Acad–Sci–USA, Apr. 16, 1996; 93(8): 3176–81.
Farhood et al., "The role of dioleoyl phosphatidylethanolamine in cationic liposome mediated gene transfer", Biochim. Biophys. Acta., May 4, 1995; 1235(2): 289–95.
Hart et al., "Lipid–Mediated Enhancement of Transfection by a Nonviral Integrin–Targeting Vector", Human Gene Therapy, (Mar. 1, 1998) 9 (4) 575–85.
Harbottle et al., "An RGD–Oligolysine Peptide: A Prototype Construct for Integrin–Mediated Gene Delivery", Human Gene Therapy, (May 1, 1998) 9 (7) 1037–47.

* cited by examiner

*Primary Examiner*—Deborah Crouch
*Assistant Examiner*—Peter Brunovskis
(74) *Attorney, Agent, or Firm*—Nixon & Vanderhye P.C.

(57) ABSTRACT

A complex that comprises (i) a nucleic acid, (ii) an integrin-binding component, for example, an integrin-binding peptide, (iii) a polycationic nucleic acid-binding component, for example, oligolysine, and (iv) a lipid component, for example, a cationic liposome, has transfection activity.

34 Claims, 6 Drawing Sheets

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 28 amino acids
      (B) TYPE: amino acid
      (C) STRANDEDNESS:
      (D) TOPOLOGY: circular (ii) MOLECULE TYPE: peptide (xi) SEQUENCE DESCRIPTION: SEQ ID NO: 1:

Gly Gly Cys Arg Gly Asp Met Phe Gly Cys Gly Gly Lys Lys Lys Lys
1               5                   10                  15

Lys Lys Lys Lys Lys Lys Lys Lys Lys Lys Lys Lys

```
            20                  25

(2) INFORMATION FOR SEQ ID NO: 2:

(i) SEQUENCE CHARACTERISTICS:
        (A) LENGTH: 27 amino acids
        (B) TYPE: amino acid
        (C) STRANDEDNESS:
        (D) TOPOLOGY: circular (ii) MOLECULE TYPE: peptide (xi) SEQUENCE DESCRIPTION: SEQ ID NO: 2:

Gly Gly Cys Arg Gly Asp Met Phe Gly Cys Gly Lys Lys Lys Lys
1               5                   10                  15

Lys Lys Lys Lys Lys Lys Lys Lys Lys Lys Lys Lys
            20                  25

(2) INFORMATION FOR SEQ ID NO: 3:

(i) SEQUENCE CHARACTERISTICS:
        (A) LENGTH: 26 amino acids
        (B) TYPE: amino acid
        (C) STRANDEDNESS:
        (D) TOPOLOGY: circular (ii) MOLECULE TYPE: peptide (xi) SEQUENCE DESCRIPTION: SEQ ID NO: 3:

Gly Gly Cys Arg Gly Asp Met Phe Gly Cys Lys Lys Lys Lys Lys
1               5                   10                  15

Lys Lys Lys Lys Lys Lys Lys Lys Lys Lys
            20                  25

(2) INFORMATION FOR SEQ ID NO: 4:

(i) SEQUENCE CHARACTERISTICS:
        (A) LENGTH: 27 amino acids
        (B) TYPE: amino acid
        (C) STRANDEDNESS:
        (D) TOPOLOGY: circular (ii) MOLECULE TYPE: peptide (xi) SEQUENCE DESCRIPTION: SEQ ID NO: 4:

Lys Lys Lys Lys Lys Lys Lys Lys Lys Lys Lys Lys Lys Lys Lys
1               5                   10                  15

Gly Ala Cys Arg Gly Asp Met Phe Gly Cys Ala
            20                  25

(2) INFORMATION FOR SEQ ID NO: 5:

(i) SEQUENCE CHARACTERISTICS:
        (A) LENGTH: 8 amino acids
        (B) TYPE: amino acid
        (C) STRANDEDNESS:
        (D) TOPOLOGY: circular (ii) MOLECULE TYPE: peptide (xi) SEQUENCE DESCRIPTION: SEQ ID NO: 5:

Cys Arg Gly Asp Met Phe Gly Cys
1               5

(2) INFORMATION FOR SEQ ID NO: 6:

(i) SEQUENCE CHARACTERISTICS:
```

(A) LENGTH: 10 amino acids
        (B) TYPE: amino acid
        (C) STRANDEDNESS:
        (D) TOPOLOGY: circular (ii) MOLECULE TYPE: peptide (xi) SEQUENCE DESCRIPTION: SEQ ID NO: 6:

Gly Gly Cys Arg Gly Asp Met Phe Gly Cys
1               5                   10

(2) INFORMATION FOR SEQ ID NO: 7:

(i) SEQUENCE CHARACTERISTICS:
        (A) LENGTH: 11 amino acids
        (B) TYPE: amino acid
        (C) STRANDEDNESS:
        (D) TOPOLOGY: circular (ii) MOLECULE TYPE: peptide (xi) SEQUENCE DESCRIPTION: SEQ ID NO: 7:

Gly Gly Cys Arg Gly Asp Met Phe Gly Cys Gly
1               5                   10

(2) INFORMATION FOR SEQ ID NO: 8:

(i) SEQUENCE CHARACTERISTICS:
        (A) LENGTH: 11 amino acids
        (B) TYPE: amino acid
        (C) STRANDEDNESS:
        (D) TOPOLOGY: circular (ii) MOLECULE TYPE: peptide (xi) SEQUENCE DESCRIPTION: SEQ ID NO: 8:

Gly Gly Cys Arg Gly Asp Met Phe Gly Cys Ala
1               5                   10

(2) INFORMATION FOR SEQ ID NO: 9:

(i) SEQUENCE CHARACTERISTICS:
        (A) LENGTH: 11 amino acids
        (B) TYPE: amino acid
        (C) STRANDEDNESS:
        (D) TOPOLOGY: circular (ii) MOLECULE TYPE: peptide (xi) SEQUENCE DESCRIPTION: SEQ ID NO: 9:

Gly Ala Cys Arg Gly Asp Met Phe Gly Cys Ala
1               5                   10

(2) INFORMATION FOR SEQ ID NO: 10:

(i) SEQUENCE CHARACTERISTICS:
        (A) LENGTH: 12 amino acids
        (B) TYPE: amino acid
        (C) STRANDEDNESS:
        (D) TOPOLOGY: circular (ii) MOLECULE TYPE: peptide (xi) SEQUENCE DESCRIPTION: SEQ ID NO: 10:

Gly Ala Cys Asp Cys Arg Gly Asp Cys Phe Cys Ala
1               5                   10

(2) INFORMATION FOR SEQ ID NO: 11:

```
        (i) SEQUENCE CHARACTERISTICS:
            (A) LENGTH: 12 amino acids
            (B) TYPE: amino acid
            (C) STRANDEDNESS:
            (D) TOPOLOGY: circular (ii) MOLECULE TYPE: peptide (xi) SEQUENCE DESCRIPTION: SEQ ID NO: 11:

Gly Ala Cys Arg Arg Glu Thr Ala Trp Ala Cys Ala
1               5                   10

(2) INFORMATION FOR SEQ ID NO: 12:

(i) SEQUENCE CHARACTERISTICS:
            (A) LENGTH: 12 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO: 12:

Gly Ala Cys Arg Arg Glu Thr Ala Trp Ala Cys Gly
1               5                   10

(2) INFORMATION FOR SEQ ID NO: 13:

(i) SEQUENCE CHARACTERISTICS:
            (A) LENGTH: 9 amino acids
            (B) TYPE: amino acid
            (C) STRANDEDNESS:
            (D) TOPOLOGY: circular (ii) MOLECULE TYPE: peptide (xi) SEQUENCE DESCRIPTION: SEQ ID NO: 13:

Cys Arg Arg Glu Thr Ala Trp Ala Cys
1               5

(2) INFORMATION FOR SEQ ID NO: 14:

(i) SEQUENCE CHARACTERISTICS:
            (A) LENGTH: 12 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO: 14:

Gly Ala Gly Pro Glu Ile Leu Asp Val Pro Ser Thr
1               5                   10

(2) INFORMATION FOR SEQ ID NO: 15:

(i) SEQUENCE CHARACTERISTICS:
            (A) LENGTH: 10 amino acids
            (B) TYPE: amino acid
            (C) STRANDEDNESS:
            (D) TOPOLOGY: circular (ii) MOLECULE TYPE: peptide (xi) SEQUENCE DESCRIPTION: SEQ ID NO: 15:

Gly Ala Cys Gln Ile Asp Ser Pro Cys Ala
1               5                   10

(2) INFORMATION FOR SEQ ID NO: 16:
```

```
    (i) SEQUENCE CHARACTERISTICS:
        (A) LENGTH: 25 amino acids
        (B) TYPE: amino acid
        (C) STRANDEDNESS:
        (D) TOPOLOGY: circular (ii) MOLECULE TYPE: peptide (xi) SEQUENCE DESCRIPTION: SEQ ID NO: 16:

Gly Ala Cys Arg Arg Glu Thr Ala Trp Ala Cys Gly Lys Gly Ala Cys
1               5                   10                  15

Arg Arg Glu Thr Ala Trp Ala Cys Gly
            20                  25
```

INTEGRIN-TARGETING VECTORS HAVING TRANSFECTION ACTIVITY

The present invention relates to an improved integrin-targeting vector that has enhanced transfection activity.

Gene therapy and gene vaccination are techniques that offer interesting possibilities for the treatment and/or prophylaxis of a variety of conditions, as does anti-sense therapy. Such techniques require the introduction of a DNA of interest into target cells. The ability to transfer sufficient DNA to specific target cells remains one of the main limitations to the development of gene therapy, anti-sense therapy and gene vaccination. Both viral and non-viral DNA delivery systems have been proposed. In some cases RNA is used instead of DNA. Receptor-mediated gene delivery is a non-viral method of gene transfer that exploits the physiological cellular process, receptor-mediated endocytosis to internalise DNA. Receptor-mediated non-viral vectors have several advantages over viral vectors. In particular, they lack pathogenicity; they allow targeted gene delivery to specific cell types and they are not restricted in the size of nucleic acid molecules that can be packaged. Gene expression is achieved only if the nucleic acid component of the complex is released intact from the endosome to the cytoplasm and then crosses the nuclear membrane to access the nuclear transcription machinery. However, transfection efficiency is generally poor relative to viral vectors owing to endosomal degradation of the nucleic acid component, failure of the nucleic acid to enter the nucleus and the exclusion of aggregates larger than about 150 nm from clathrin coated vesicles.

Integrins are a super-family of heterodimeric membrane proteins consisting of several different α and β subunits. They are important for attachment of cells to the extracellular matrix; cell-cell interactions and signal transduction. Integrin-mediated cell entry is exploited for cell attachment and entry by a number of intracellular pathogens including *Typanosoma cruzi* (Fernandez et al., 1993), adenovirus (Wickham et al., 1993), echovirus (Bergelson et al., 1992) and foot-and-mouth disease virus (Logan et al., 1993) as well as the enteropathogen Y. pseudotuberculosis (Isberg, 1991). Egg-sperm fusion is also integrin mediated. Intensive study of the invasin-integrin mediated internalisation process of *Yersinia pseudotuberculosis* demonstrated that, for efficient cell entry, integrin-binding ligands should have a high binding affinity and a non-polar distribution (Isberg, 1991). Integrin-mediated internalisation proceeds by a phagocytic-like process allowing the internalisation of bacterial cells one to two micrometers in diameter (Isberg, 1991). Targeting of non-viral vectors to integrins, therefore, has the potential to transfect cells in a process that mimics infection of cells by pathogens and avoids the size limitation imposed by clathrin-coated vesicles in receptor-mediated endocytosis.

A further advantage of integrin-mediated vectors is that a large number of peptide ligands for integrin receptors have been described, including sequences derived from natural protein ligands [Verfaille, 1994 #635; Wang, 1995 #645; Staatz, 1991 #539; Pierschbacher, 1984 #314; Massia, 1992 #86, Clements et al. 1994 & Lu et al, 1993] or selected from phage display libraries (Koivunen et al. 1995; 1993; 1994; O'Neil et al. 1992; Healy et al 1995; Pasqualani et al. 1995).

The conserved amino acid sequence arginine-glycine-aspartic acid (RGD) is an evolutionarily conserved feature of many, but not all, natural integrin-binding ligands such as extracellular matrix proteins and viral capsids. Peptides, particularly those containing cyclic-RGD domains can also bind integrins. Peptides containing cyclic-RGD domains are particularly suitable ligands for vectors since they bind to integrins with higher affinities than linear peptides (Koivunen et al. 1995). Hart et al. have demonstrated previously that multiple copies of a cyclic RGD peptide displayed in the major coat protein subunit of fd filamentous phage particles, approximately 900 nm in length, are internalised efficiently by cells in tissue culture in an integrin-mediated manner (Hart et al., 1994). The phage particles were probably internalised by a phagocytic-like process as their size would exclude them from endocytosed vesicles (Hart et al., 1994).

The cyclic RGD-containing peptide GGCRGDMFGCGG[K]$_{16}$ [SEQ.ID.NO.:1] was synthesised with a sixteen-lysine tail for complex formation with plasmid DNA (Hart et al., 1995). Significant levels of integrin-mediated gene expression were achieved in epithelial cell lines with the vector GGCRGDMFGCG[K]$_{16}$ [SEQ.ID.NO.:2] (Hart et al., 1995) and the vectors GGCRGDMFGC[K]$_{16}$ [SEQ.ID.NO.:3] (WO96/15811). A similar peptide [K]$_{16}$GACRGDMFGCA [SEQ.ID.NO. :4], which has the sixteen-lysine domain at the N-terminus and which is easier to synthesise than the prototype peptide (WO96/15811 and Hart et al., 1997) generated better transfection levels. Integrin mediated gene expression was generally achieved at levels of about 1 to 10%. The presence of chloroquine in the transfection medium gave some enhancement of transfection in some but not all cell lines tested.

The present invention is based on the surprising observation that inclusion of a lipid component in the oligolysine/-peptide/DNA complex increases levels of transfection of DNA from about 1 to 10% to about 50 to almost 100%. Not only is the level of transfection increased dramatically but, contrary to previous experience, the increase is observed in all cell lines tested, including endothelial, epithelial and tumour cell lines.

The present invention provides a complex that comprises (i) a nucleic acid, especially a nucleic acid encoding a sequence of interest, (ii) an integrin-binding component, (iii) a polycationic nucleic acid-binding component, and (iv) a lipid component.

The complex is a transfection vector.

The nucleic acid may be obtained from natural sources, or may be produced recombinantly or by chemical synthesis. It may be modified, for example, to comprise a molecule having a specific function, for example, a nuclear targeting molecule. The nucleic acid may be DNA or RNA. DNA may be single stranded or double stranded. The nucleic acid may be suitable for use in gene therapy, in gene vaccination or in anti-sense therapy. The nucleic acid may be or may relate to a gene that is the target for particular gene therapy or may be a molecule that can function as a gene vaccine or as an anti-sense therapeutic agent. The nucleic acid may be or correspond to a complete coding sequence or may be part of a coding sequence.

Alternatively, the nucleic acid may encode a protein that is commercially useful, for example industrially or scientifically useful, for example an enzyme; pharmaceutically useful, for example, a protein that can be used therapeutically or prophylactically as a medicament or vaccine; or diagnostically useful, for example, an antigen for use in an ELISA. Host cells capable of producing commercially useful proteins are sometimes called "cell factories".

Appropriate transcriptional and translational control elements are generally provided. For gene therapy, the nucleic acid component is generally presented in the form of a nucleic acid insert in a plasmid or vector. In some cases, however, it is not necessary to incorporate the nucleic acid component in a vector in order to achieve expression. For example, gene vaccination and anti-sense therapy can be achieved using a naked nucleic acid.

The nucleic acid is generally DNA but RNA may be used in some cases, for example, in cancer vaccination. The nucleic acid component is referred to below as the plasmid component or component "ED".

The integrin-binding component is any component that is capable of binding specifically to integrins found on the surface of cells. The integrin-binding component may be a naturally occurring integrin-binding ligand, for example, an extra-cellular matrix protein, a viral capsid protein, the bacterial protein invasin, a snake venom disintegrin protein, or an integrin-binding fragment of any such protein. Such integrin-binding proteins and fragments thereof may be obtained from natural sources or by recombinant techniques, but they are difficult to synthesise and purify in large amounts, they require conjugation directly to DNA or RNA or to polycationic elements for DNA or RNA binding, and are immunogenic in vivo.

It is preferable to use integrin-binding peptides, in particular because of their ease of synthesis, purification and storage, their potential for chemical modification, and their potentially low immunogenicity in vivo. Examples of integrin-binding peptides are given in Verfaille, 1994 #635; Wang, 1995 #645; Staatz, 1991 #539; Pierschbacher, 1984 #314; Massia, 1992 #86, Clements et al. 1994 & Lu et al, 1993; and in Koivunen et al. 1995; 1993; 1994; O'Neil et al. 1992; Healy et al 1995; and Pasqualani et al. 1995.

As indicated above, peptides containing the conserved amino acid sequence arginine-glycine-aspartic acid (RGD) bind with high affinity to integrins. Accordingly, peptides comprising the RGD sequence are particularly useful. The affinity between integrin and peptide ligands is influenced by the amino acid sequence flanking the RGD domain. Peptides having a cyclic region in which the conformational freedom of the RGD sequence is restricted generally have a higher affinity for integrin receptors than do their linear counterparts. Such cyclic peptides are particularly preferred. Cyclic peptides may be formed by the provision of two cysteine residues in the peptide, thus enabling the formation of a disulphide bond. A cysteine residue may be separated from the RGD sequence by one or more residues, for example, up to six residues, or may be immediately adjacent to the RGD sequence, although preferably both cysteines are not immediately adjacent to the ends of the RGD sequence.

An example of an amino acid sequence that will permit cyclisation by disulphide bond formation is CRGDMFGC [SEQ.ID.NO.:5]. A peptide that consists of or comprises the sequence CRGDMFGC may advantageously be used as an integrin-binding peptide according to the present invention. Examples of peptides that comprises the sequence CRGD-MFGC and that are effective integrin-binding ligands are the peptides GGCRGDMFGC [SEQ.ID.NO.:6], GGCRGDMF-GCG [SEQ.ID.NO.:7], GGCRGDMFGCA [SEQ.ID.NO.:8] and GACRGDMFGCA [SEQ.ID.NO.:9].

The peptide GACDCRGDCFCA [SEQ.ID.NO.:10] has the potential to form two disulphide bonds for stabilising the RGD loop. That peptide and others having the potential to form two RGD-stabilising disulphide bonds, may be particularly useful as integrin-binding ligands according to the present invention.

However, not all integrin-binding peptides contain the conserved RGD sequence. For example, the peptides GACRRETAWACA [SEQ.ID.NO.:11] and GACRRE-TAWACG [SEQ.ID.NO.:12] are integrin-specific peptides. Other peptides comprising the sequence CRRETTAWAC [SEQ.ID.NO.:13] may be used, as may other non-RGD peptides, particularly those that have the potential for disulphide bond formation.

Peptide sequences may be designed on the basis of known ligands, for example, on the basis of integrin-binding domains of naturally-occurring integrin-binding ligands, or on the basis of known peptides that bind to integrins.

As stated above integrins are a family of heterodimeric proteins found on the surface of cells. They consist of several different α and β subunits. Some integrins are found on may types of cells, others are more specific, for example, α5 and αv integrins are widespread and are found on a diverse range of cells. Integrin-binding ligands can vary in their affinity for different integrins. For example, GACRGD-MFGCA [SEQ.ID.NO.:9] (peptide 1) has affinity for α5 and αv integrins but is non-specific (O'Neil et al. 1992, Hart et al. 1997). GACDCRGDCFCA [SEQ.ID.NO.:10] (peptide 5) has high affinity for integrin αv but is not αv-specific (Koivunen et al. 1995; Hart et al. 1997). GACRRE-TAWACG [SEQ.ID.NO.:12] (peptide 6) however, which does not contain the conserved RGD region, is α5β1-specific (Koivunen et al. 1995). Various integrin-binding peptides and their integrin specificity are set out in the Table below:

TABLE

| Peptide number and integrin specificity | Sequence | SEQ.ID.NO. |
|---|---|---|
| Peptide 1 (αv, α5β1) | GACRGDMFGCA | SEQ.ID.NO.:9 |
| Peptide 2 (αv, α5β1) | GACRGDMFGCGG | SEQ.ID.NO.:12 |
| Peptide 5 (αv) | GACDCRGDCFCA | SEQ.ID.NO.:10 |
| Peptide 6 (α5β1) | GACRRETAWACG | SEQ.ID.NO.:12 |
| Peptide 7 (α4β1) | GAGPEILDVPST | SEQ.ID.NO.:14 |
| Peptide 8 (α4β1) | GACQIDSPCA | SEQ.ID.NO.:15 |
| Peptide 9 (α5β1) | GACRRETAWACGKGACRRETAWACG | SEQ.ID.NO.:16 |

It should be noted that the use of a lipid component according to the present invention greatly enhances transfection for all peptides and all cell types tested, unlike other enhancement techniques that have been tried, for example, chloroquine, which enhance transfection to a small extent in some but not all cell types tested.

The polycationic nucleic acid-binding component is any polycation that is capable of binding to DNA or RNA. The polycation may have any number of cationic monomers provided the ability to bind to DNA or RNA is retained. For example, from 3 to 100 cationic monomers may be present, for example, from 10 to 20, especially about 16. An oligolysine is particularly preferred, for example, having from 10 to 20 lysine residues, for example, from 15 to 17 residues, especially 16 residues i.e. $[K]_{16}$.

The polycationic DNA or RNA-binding component may advantageously be linked or otherwise attached to the integrin-binding component. A combined integrin-binding component/polycationic DNA or RNA-binding component may be referred to below as component "I". For example, a polycationic DNA or RNA-binding component may be chemically bonded to an integrin-binding component, for example, by a peptide bond in the case of an oligolysine. The polycationic component may be linked at any position of the integrin-binding component. Preferred combinations of integrin-binding component and polycationic DNA or RNA-binding component are an oligolysine, especially $[K]_{16}$, linked via a peptide bond to a peptide, for example, a peptide as described above.

The lipid component may be or or may form a cationic liposome. The lipid component may be or may comprise one or more lipids selected from cationic lipids and lipids having membranae destabilising or fusogenic properties, especially a combination of a cationic lipid and a lipid that has membrane destabilising properties.

A preferred lipid component ("L") is or comprises the neutral lipid dioleyl phosphatidylethanolamine, referred to herein as "DOPE". DOPE has membrane destabilising properties sometimes referred to as "fusogenic" properties (Farhood et al. 1995). Other lipids, for example, neutral lipids, having membrane destabilising properties, especially membrane destabilising properties like those of DOPE may be used instead of or as well as DOPE.

Other phospholipids having at least one long chain alkyl group, for example, di(long alkyl chain)phospholipids may be used. The phospholipid may comprise a phosphatidyl group, for example, a phosphatidylalkanolamine group, for example, a phosphatidylethanolamine group.

A further preferred lipid component is or comprises the cationic lipid N-[1-(2,3-dioleyloxy)propyl]-N,N,N-trimethylammonium chloride, referred to herein as "DOTMA". DOTMA has cationic properties. Other cationic lipids may be used in addition to or as an alternative to DOTMA, in particular cationic lipids having similar properties to those of DOTMA. Such lipids are, for example, quaternary ammonium salts substituted by three short chain alkyl groups, and one long chain alkyl group. The short chain alkyl groups may be the same or different, and may be selected from methyl and ethyl groups. At least one and up to three of the short chain alkyl group may be a methyl group. The long alkyl chain group may have a straight or branched chain, for example, a di(long chain alkyl)alkyl group.

Another preferred lipid component is or comprises the lipid 2,3-dioleyloxy-N-[2-(spermidinecarboxamido)ethyl]-N,N-dimethyl-1-propanaminiumtrifluoridoacetate, referred to herein as "DOSPA". Analogous lipids may be used in addition to or as an alternative to DOSPA, in particular lipids having similar properties to those of DOSPA. Such lipids have, for example, different short chain alkyl groups from those in DOSPA.

A preferred lipid component comprises DOPE and one or more other lipid components, for example, as described above. Especially preferred is a lipid/component that comprises a mixture of DOPE and DOTMA. Such mixtures form cationic liposomes. An equimolar mixture of DOPE and DOTMA is found to be particularly effective. Such a mixture is known generically as "lipofectin" and is available commercially under the name "Lipofectin". The term "lipofectin" is used herein generically to denote an equimolar mixture of DOPE and DOTMA. Other mixtures of lipids that are cationic liposomes having similar properties to lipofectin may be used. Lipofectin is particularly useful as it is effective in all cell types tested.

A further preferred lipid component comprises a mixture of DOPE and DOSPA. Such mixtures also form cationic liposomes. A mixture of DOPE and DOSPA in a ratio by weight 3:1 DOSPA:DOPE is particularly effective. Such a mixture, in membrane filtered water, is available commercially under the name "Lipofectamine". Mixtures comprising DOPE, DOTMA and DOSPA may be used, for example, mixtures of lipofectin and lipofectamine.

Other cationic lipids are available commercially, for example, DOTAP (Boehringer-Mannheim) and lipids in the Tfx range (Promega). DOTAP is N-[1-(2,3-diolyloxy)propyl]-N,N,N-tri-methylammonium methylsulphate. The Tfx reagents are mixtures of a synthetic cationic lipid [N,N,N',N'-tetramethyl-N,N'-bis(2-hydroxyethyl)-2,3-di(oleoyloxy)-1,4-butanediammonium iodide and DOPE. All the reagents contain the same amount of the cationic lipid component but contain different molar amounts of the fusogneic lipid, DOPE.

However, lipofectin and lipofectamine appear to be markedly more effective as the lipid component in LID complexes of the present invention than are DOTPA and Tfx agents.

The effectiveness of a putative integrin-binding component, polycationic DNA or RNA-binding component, or of lipid component may be determined readily using the methods described herein.

The efficiency of transfection using a complex of the invention is influenced by the ratio lipid component:integrin-binding component:DNA or RNA. For any chosen combination of components for any particular type of cell to be transfected, the optimal ratios can be determined simply by admixing the components in different ratios and measuring the transfection rate for that cell type, for example, as described herein.

For example, a combination consisting of a pGL2 plasmid, which is a plasmid encoding luciferase (a reporter gene) under an SV40 promoter as DNA component (D), $[K]_{16}$GACRGDMFGCA [SEQ.ID.NO.:17] ($[K]_{16}$-peptide 1) as a combined integrin-binding component/polycationic DNA binding component (I), and lipofectin (DOPE:DOTMA 1:1 molar ratio) as the lipid component (L) was tested to find the optimal ratio of components. Complexes formed with 1 μg of lipofectin (L) and 4 μg of $[K]_{16}$-peptide (I) per 1 μg of plasmid (D) were 100-fold more active than complexes lacking lipofectin. Addition of larger amounts of lipofectin reduced transfection activity in a lipofectin dose-dependent manner.

An optimal transfection ratio of 0.75 μg of lipofectin (L) per 4 μg of the $[K]_{16}$-peptide integrin-binding component/poly-cationic DNA or RNA-binding component (I) per 1 μg plasmid DNA or RNA (nucleic acid component, D) was found for three different cell lines namely melanoma cell, endothelial cells and epithelial cells. That ratio was subsequently found to be effective for other different cell lines and for other oligolysine-peptides. A ratio L:I:D of 0.75:4:1 by weight corresponds to a molar ratio of 0.5 nmol lipofectin: 1.25 nmol $[K]_{16}$ -peptide 6: 0.25 pmol plasmid pGL2-control. A ratio L:I:D of 0.75:4:1 by weight, or the corresponding molar ratio are preferred when lipofectin is used as the lipid component.

For a combination of components in which lipofectin is replaced by lipofectamine (DOPE/DOSPA), the optimal ratio was found to be 12 μg lipofectamine: 4 μg $[K]_{16}$- peptide 6: 1 μg plasmid DNA or RNA. A ratio of L:I:D of 12:4:1 by weight, or the corresponding molar ratio, is appropriate for lipofectamine-containing complexes. Optimal ratios for other systems may be determined analogously.

Lipofectin and lipofectamine appear to be particularly effective in enhancing transfection. Lipofectin has the advantage that only very small amounts are required. Any side effects that may occur are therefore minimised. As indicated above, the optimal weight ratio of components L:I:D when using lipofectamine is 12:4:1. With lipofectin the optimal ratio is only 0.75:4:1.

The present invention provides a process for the production of a transfection complex of the present invention, which comprises admixing components (i), (ii), (iii) and (iv).

Although the components may be admixed in any order, it is generally preferable that the lipid component is not added last. In the case where there is a combined integrin-binding component/polycationic DNA or RNA-binding component it is generally preferable to combine the components in the following order: lipid component; combined integrin-binding/polycationic DNA or RNA-binding component; DNA or RNA component, for example, in the order: lipofectin, oligolysine-peptide component, DNA or RNA component.

The present invention also provides a mixture comprising an integrin-binding component, a polycationic nucleic acid-binding component, and a lipid component.

Such a mixture may be used to produce a nucleic acid-containing transfection complex of the invention by the incorporation of a nucleic acid with the mixture, for example, by admixture. Alternatively, the mixture of the invention may be used for the production of a complex which comprises, instead of the nucleic acid component, any other component that is capable of binding to the polycationic nucleic-acid binding component, for example, a protein.

The present invention further provides a process for the production of a complex of the present invention, which comprises admixing a nucleic acid with a mixture of the invention.

The individual components of a mixture of the invention are each as described above in relation to the complex of the invention. The preferred components, preferred combinations of components, preferred ratios of components and preferred order of mixing, both with regard to the mixture and to the production of a complex, are as described above in relation to the complex of the invention.

A mixture of the present invention preferably comprises an equimolar mixture of DOPE and DOTMA (lipofectin) as the lipid component and an oligolysine-peptide especially a $[K]_{16}$-peptide as a combined integrin-binding/nucleic acid-binding component. The preferred molar ratio lipofectine:oligolysine-peptide is 0.75:4.

The present invention provides a method of transfecting a cell with a nucleic acid, which comprises contacting the cell in vitro or in vivo with a complex of the present invention.

The present invention also provides a process for expressing a nucleic acid in a host cell, which comprises bringing the cell into contact with a complex of the present invention. The host cell is then cultured under conditions that enable the cell to express the nucleic acid.

The present invention further provides a process for the production of a protein, which comprises contacting a host cell in vitro or in vivo with a complex of the present invention, allowing the cell to express the protein, and obtaining the protein. The host cell may be transfected in vitro with a nucleic acid by means of a complex of the present invention and cultured, the protein being obtained either from the host cell or from the culture medium.

The present invention further provides a cell transfected with a complex of the present invention, and also the progeny of such a cell.

The present invention also provides a pharmaceutical composition which comprises a complex of the present invention in admixture or conjunction with a pharmaceutically suitable carrier. The composition may be a vaccine.

The present invention also provides a method for the treatment or prophylaxis of a condition caused in a human or in a non-human animal by a defect and/or a deficiency in a gene, which comprises administering a complex of the present invention to the human or to the non-human animal.

The present invention also provides a method for therapeutic or prophylactic immunisation of a human or of a non-human animal, which comprises administering a complex of the present invention to the human or to the non-human animal.

The present invention also provides a method of anti-sense therapy of a human or of a non-human animal, wherein a complex of the present invention comprising anti-sense DNA is administered to the human or to the non-human animal.

The present invention further provides a complex of the present invention for use as a medicament and/or vaccine, for example for the prophylaxis of a condition caused in a human or in a non-human animal by a defect and/or a deficiency in a gene, for therapeutic or prophylactic immunisation of a human or of a non-human animal, or for anti-sense therapy of a human or of a non-human animal.

The present invention also provides the use of a complex of the present invention for the manufacture of a medicament for the prophylaxis of a condition caused in a human or in a non-human animal by a defect and/or a deficiency in a gene, for therapeutic or prophylactic immunisation of a human or of a non-human animal, or for anti-sense therapy of a human or of a non-human animal.

A non-human animal is, for example, a mammal, bird or fish, and is particularly a commercially reared animal.

The DNA or RNA in the complex of the invention is appropriate for the intended gene therapy, gene vaccination, or anti-sense therapy. The DNA or RNA and hence the complex is administered in an amount effective for the intended purpose.

In a further embodiment, the present invention provides a kit suitable for preparing a mixture of the present invention. Such a kit comprises the following: (i) an integrin-binding component; (ii) a polycationic nucleic acid-binding component, and (iii) a lipid component.

A kit suitable for producing a complex of the present invention may comprise components (i) to (iii) above and (iv) either a nucleic acid or a plasmid or vector suitable for the expression of a nucleic acid, the plasmid or vector being either empty or comprising the nucleic acid.

The components of a kit are, for example, as described above in relation to a complex or a mixture of the present invention. Preferred copmonents are as described above.

A kit generally comprises instructions for the production of a complex or a mixture of the present invention. The instructions preferably indicate the preferred ratios of the components and the preferred order of admixing the components, for example, as described above. A kit may be used for producing a complex suitable for gene therapy, gene vaccination or anti-sense therapy. Alternatively, it may be used for producing a complex suitable for transfecting a host cell with a nucleic acid encoding a commercially useful protein i.e. to produce a so-called "cell factory".

The kit of the present invention enables the user to produce quickly and easily a highly efficient transfection complex of the present invention using any DNA or RNA of choice.

A kit of the invention may comprises the following components: (a) an integrin-binding component, (b) a polycationic nucleic acid-binding component, (c) a lipid component and (d) a nucleic acid.

Such a kit is suitable for the production of a complex for use, for example, in gene vaccination or anti-sense therapy.

In a kit of the invention the components including the preferred components are, for example, as described above in relation to a complex of the present invention.

The present invention also provides a lipid component as described above for use in increasing the efficiency of transfection of a cell with a nucleic acid, either DNA or RNA, the lipid component being used in combination with an integrin-binding component and a polycationic nucleic acid-binding component.

The present invention also provides the use of a lipid component as described above for the manufacture of a medicament comprising (i) a nucleic acid, especially a nucleic acid encoding a sequence of interest, (ii) an integrin-binding component, (iii) a polycationic nucleic acid-binding component and (iv) the lipid component.

The medicament may be for gene therapy, gene vaccination, or anti-sense therapy.

The present invention also provides a transfection complex that comprises (i) a nucleic acid, especially a nucleic acid encoding a sequence of interest, (ii) an integrin-binding component, and (iii) a polycationic a nucleic acid-binding component, characterised in that a lipid component, for example as described above, is an additional component of the complex.

The present invention also provides a method for increasing the efficiency of a transfection vector that comprises (i) a nucleic acid, especially a nucleic acid encoding a sequence of interest, (ii) an integrin-binding component, and (iii) a polycationic a nucleic acid-binding component, characterised in that a lipid component, for example as described above, is incorporated as an additional component of the complex.

In each case, the various components are as described above. The lipid component is, for example, a mixture of DOPE and DOSPA or, especially, a mixture of DOPE and DOTMA, in particular an equimolar mixture of DOPE and DOTMA (lipofectin).

Targets for gene therapy are well known and include monogenic disorders, for example, cystic fibrosis, various cancers, and infections, for example, viral infections, for example, with HIV. For example, transfection with the p53 gene offers great potential for cancer treatment. Targets for gene vaccination are also well known, and include vaccination against pathogens for which vaccines derived from natural sources are too dangerous for human use and recombinant vaccines are not always effective, for example, hepatitis B virus, HIV, HCV and herpes simplex virus. Targets for anti-sense therapy are also known. Further targets for gene therapy and anti-sense therapy are being proposed as knowledge of the genetic basis of disease increases, as are further targets for gene vaccination.

Transfection complexes of the present invention have been demonstrated to transfect various different cell types, including endothelial and epithelial cells, and tumour cells. Transfection of all cell types tested including cell types that are particularly reistant to transfection with most plasmid transfection vectors, for example, neuroblastoma cells, primary smooth muscle cells and cardiac myocytes, and haematopoieic cells has been achieved with high efficiency using transfection complexes of the present invention. This enables effective gene therapy, gene vaccination and antisense therapy without the previous restrictions as to cell type. For example, transfection with the p53 gene for cancer therapy has great potential but is currently limited by the range of cell types in which effective transfection can be achieved.

The effective tranfection of neuroblastoma cells demonstrates that the complexes of the invention may be used as vaccines or for therapy of neuroblastoma, an important childhood malignancy. The effective transfection of primary smooth muscle cells and cardiac myocytes, which are particularly resistant to plasmid-mediated transfection, demonstrates that diseases and other pathological conditions affecting muscles and the cardiovascular system can now be treated by gene therapy. One such condition is restenosis. After balloon angioplasty plaques reform in 30–50% of cases. A gene that prevents proliferation of cells in blood vessel walls may be introduced using a complex of the present invention to reduce restenosis.

Haematopoietic cells are another cell type that is particularly resistant to plasmid-mediated transfection. The effectiveness of tranfection using a complex of the present invention, which can exceed 60%, now enables gene therapy, gene vaccination and anti-sense therapy of diseases involving haematopoietic cells, including leukaemia and bone marrow stem cell disorders. For example, transfection of a cytokine gene may be used for adjuvant immunotherapy.

Complexes of the invention have been demonstrated to be effective vectors for intracellular transport and delivery of anti-sense oligonucleotides, which enables antiviral and cancer therapy.

Furthermore, complexes of the invention have been demonstrated to be effective for intracellular transport of very large DNA molecules, for example, DNA larger than 125kb, which is particularly difficult using conventional vectors. This enables the introduction of artificial chromosomes into cells.

Transfection at high levels has been demonstrated in vivo, confirming the utility of the complexes of the invention for gene therapy, antisense therapy and gene vaccination. Transfection of the airways, for example, the bronchial epithelium demonstrates utility for gene therapy of, for example, cystic fibrosis and asthma. Transfection of corneal endothelium demonstrates utility for treatment of eye disease affecting the cornea or corneal organ transplants, for example in glaucoma.

The high levels of transfection make the complex of the invention particularly suitable for the production of host cells capable of producing a desired protein, so-called "cell factories". For long-term production, it is desirable that the introduced nucleic acid is incorporated in the genome of the host cell, or otherwise stably maintained. That can be readily ascertained. As indicated above, the range of proteins produced in this way is large, including enzymes for scientific and industrial use, proteins for use in therapy and prophylaxis, immunogens for use in vaccines and antigens for use in diagnosis.

The present invention provides a non-viral vector that is capable of high efficiency transfection. In a preferred embodiment, the vector comprises four modular elements; an oligolysine, especially $[K]_{16}$, DNA or RNA-binding element; a high affinity integrin-binding peptide, for example, a peptide described herein; a DNA or RNA sequence, optionally in a plasmid, and optionally regulated by a viral promoter and an enhancing element; the cationic liposome DOTMA/DOPE (lipofectin). The combination of oligolysine-peptide/DNA or RNA complex with the cationic liposome formulation DOTMA/DOPE is a potent combination. Alternatively a DOPE/DOSPA formulation may be used instead of or in addition to a DOTMA/DOPE formulation. The optimisation of variables associated with complex formation and the mode of transfection by LID complexes has been demonstrated. In addition, analysis by atomic forces microscopy has been carried out to assess the structure of the complexes.

The most important variables in the formation of optimal LID transfection complexes appear to be the ratio of the three components and their order of mixing. The same composition appears to be optimal for all cell lines tested.

The mechanism of action of the complex of the present invention, the reason for the unexpectedly high levels of transfection and the surprisingly wide variety of cells that can be transfected at that high efficiency are not yet understood.

However, the following observations made as a result of the present invention indicate that the role of the lipid component is to enhance the efficiency of transfection mediated by oligolysine-peptide/DNA or RNA complexes:

The level of transfection with LID (lipofectin/$[K]_{16}$-peptide/plasmid) complexes is three to six fold higher than that with LKD (lipofectin/$[K]_{16}$/plasmid) complexes prepared with the same charge ratios, or with LD (lipofectin/plasmid) complexes. This indicates that the integrin-targeting moiety, i.e. the peptide, is a significant factor in the transfection efficiency of those complexes.

Optimised LID transfection complexes contain only one seventh of the amount of lipofectin required for optimal transfection with LD complexes. Transfections with low-ratio LD complexes that contain the same ratio of lipofectin to $[K]_{16}$-peptide/-plasmid as in optimal LID complexes but no $[K]_{16}$-peptide, did not transfect cells at all. This suggests that the role of lipofectin in LID complexes is to enhance transfection mediated by the integrin receptor-binding peptide.

Furthermore, we have found that both LID and ID complexes both form spherical particles of similar sizes. Optimal LD complexes, however, formed a tubular network with some tubule-associated particles, which suggests a different type of cellular interaction and transfection mechanism from LID and ID transfections.

It is possible that condensation of plasmid DNA or RNA by the oligolysine element of the integrin-targeting oligolysine-peptides and the cationic charge of the complexes may lead to high levels of expression when associated with lipofectin, and the integrin targeting moiety i.e. the peptide is irrelevant. Transfection experiments with LKD complexes, mixed in the same order and the same charge ratios as the LID complexes, were more efficient than LD or KD complexes. To assess the contribution of the relative importance of the oligolysine element and the integrin-targeting peptide domain of the combined integrin-binding component/polycationic DNA or RNA-binding component I, transfection by LID complexes were prepared containing a range of proportions of $[K]_{16}$ and $[K]_{16}$integrin targeting peptide 6, $[K]_{16}$GACRRETAWACG [SEQ.ID.NO.:18]. Transfection expression data indicate higher,efficiencies with complexes in which increasing amounts of $[K]_{16}$peptide 6 replace $[K]_{16}$ and a dose-dependency on the amount of integrin-targetting (ligand-binding) domain i.e. peptide 6.

The ratio of components mixed together to form the optimal transfection complex is also informative as to the possible mechanism of lipofectin mediated enhancement. The DOTMA element of lipofectin is cationic, which may enhance the activity of the complex, while DOPE may have the ability to destabilise the endosomal membrane (Farhood et al., 1995) enhancing endosomal release of plasmid DNA or RNA. The components of the LID complexes are mixed together in constant optimal ratios. It is assumed that the particles formed also contain these elements in the same proportions. Therefore, 3 nmol negative charge from plasmid DNA or RNA are associated with approximately 21 nmol positive charge from the $[K]_{16}$-peptide. Lipofectin, however, provides only a further 0.25 nmol of positive charge. This suggests that, contrary to expectations, the enhancing effect of lipofectin in LID complexes is not charge related but may relate to the membrane destabilising effect of the DOPE component.

While not limited to the following theory of the mechanism of action, the following model of the early stages of the transfection process, which is based on the observations described herein, is proposed to explain the surprising and unexpected high efficiency of transfection by LID complexes, which high efficiency is found in all the cell types investigated.

The complexes are formed electrostatically by random association of lipofectin, oligolysine-peptide and plasmid DNA or RNA. The relative high proportion of oligolysine-peptide ensures a high proportion of integrin-targeting ligands per plasmid molecule. Particles are formed that contain one or more plasmids, associated with thousands of oligolysine-peptides and, therefore, a very high concentration of integrin-targeting ligands. By mixing lipofectin with the oligolysine-peptide, then adding plasmid DNA or RNA complexes are formed containing all three components. The particles, due to the high density of ligands, have a high avidity for integrins on cell surfaces, bind and are internalised by a phagocytic process (Hart et al., 1994). The vesicles fuse to form endosomes where, under acid conditions, the DOPE element contained within the particles mediates destabilisation of the endosomal membrane and subsequent plasmid release into the cytoplasm. Phagocytosed particles lacking lipofectin are degraded in the endosomes. Particles lacking the integrin-targeting moiety are less efficient at cell binding and internalisation. Both lipofectin and the oligolysine ($[K]_{16}$) element of the oligolysine-peptides probably contribute to the overall efficiency of the LID complexes but the integrin-targeting capacity of the oligolysine/peptide component appears to be important for optimal targeting and internalisation of the complexes.

The following non-limiting Examples illustrate the present invention. The Examples refer to the accompanying drawings, in which.

Figure 4:
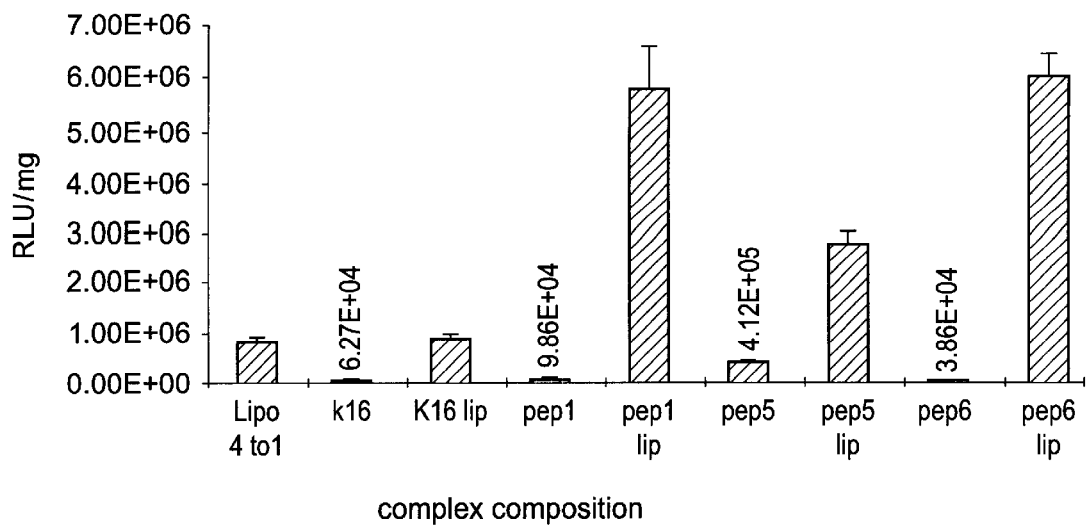

FIG. 4 shows a comparison of enhancement of transfection by lipofectin of complexes containing plasmid pGL2 and oligolysine-peptide 1 ($[K]_{16}$GACRGDMFGCA, pep 1), or oligolysine-peptide ($[K]_{16}$GACDCRGDCFCA [SEQ.ID.No.:20], pep 5), or oligolysine-peptide 6 ($[K]_{16}$GACRRETAWACG [SEQ.ID.NO.:18], pep 6) or $[K]_{16}$ (K16), with lipofectin (lip) and without lipofectin, and a complex containing plasmid pGL2 with lipofectin:$[K]_{16}$lysine-peptide 1 in a ratio by weight of 4:1 (Lipo 4 to 1).

Figure 5:
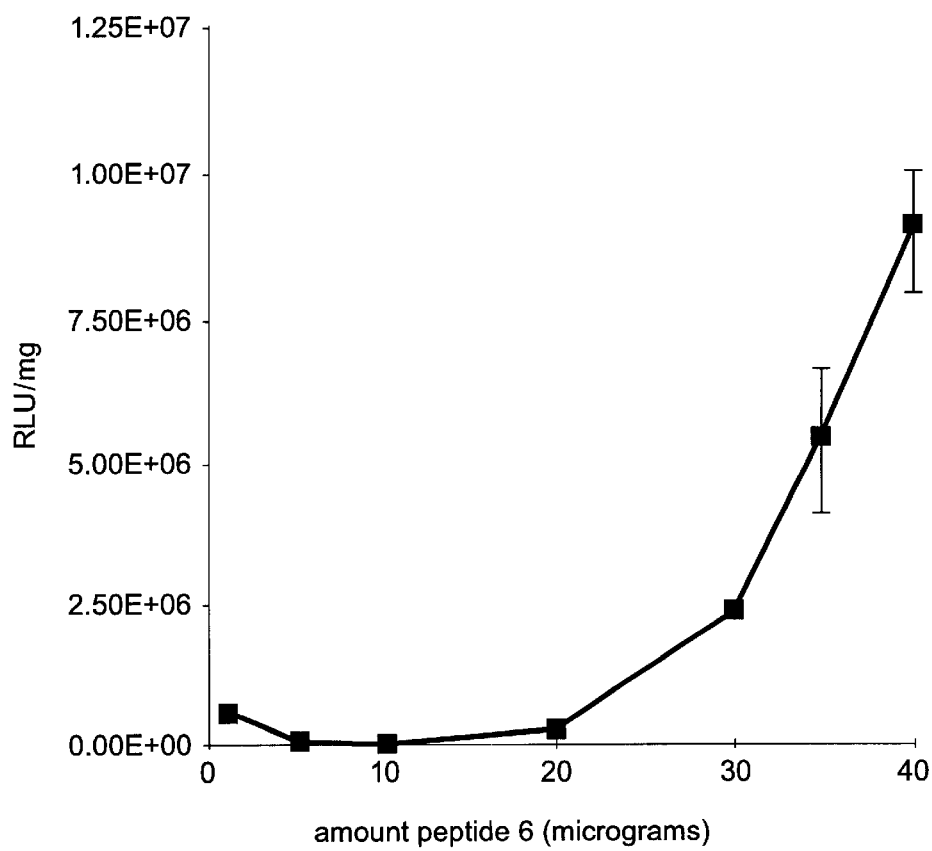

FIG. 5 shows the dose-dependency of a complex containing lipofectin, oligolysine-peptide 6 ($[K]_{16}$GACRRETAWACG) and plasmid pGL2 on the availability of integrin-binding ligands.

Figure 6:
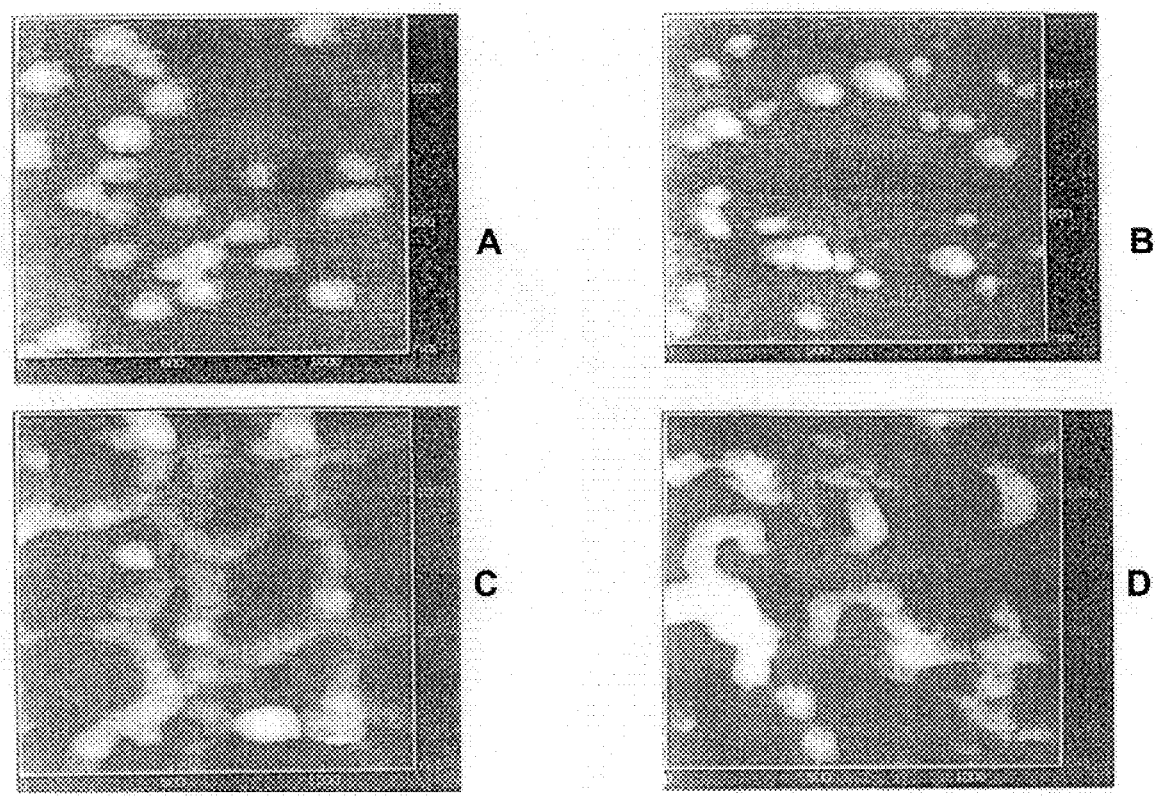

FIG. 6 shows the structure of various complexes, as determined using atomic force microscopy, the complexes being formed with different combinations of plasmid DNA (plasmid pGL2), oligolysine-peptide ($[K]_{16}$-peptide 6) and lipofectin as follows: A: $[K]_{16}$-peptide 6 and plasmid pGL2; B: $[K]_{16}$-peptide 6, lipofectin and plasmid pGL2; C: lipofectin and plasmid pGL2, optimal ratio; D: lipofectin and plasmid pGL2, suboptimal ratio.

Figure 7:
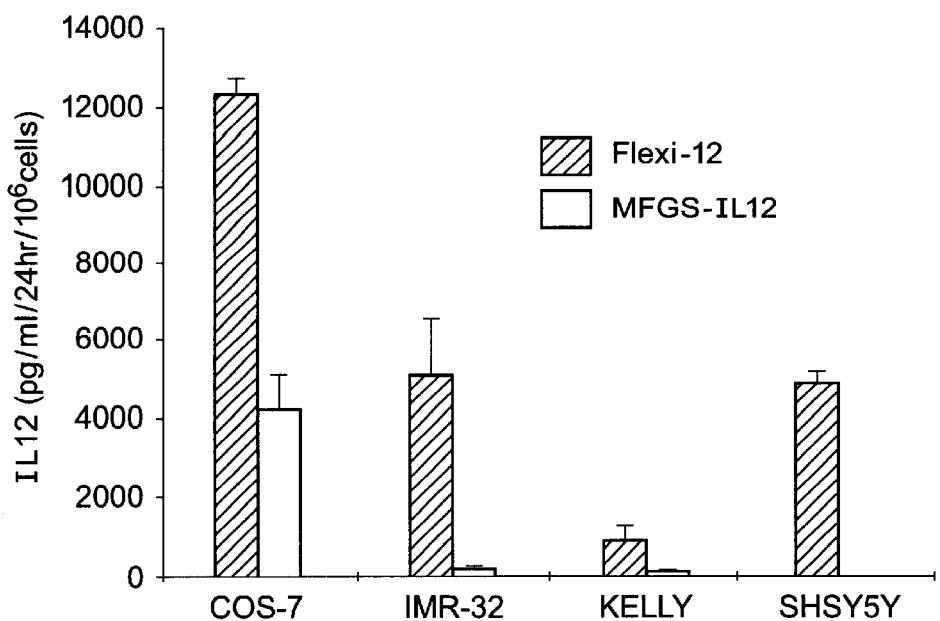

FIG. 7 shows levels of expression of IL-12 48 hours after transfection of COS-7 cells and neuroblastoma cells lines IMR-32, KELLY and SHSY-5Y with a complex containing lipofectin, oligolysine-peptide 6 ($[K]_{16}$GACRRETAWACG) and either two retroviral plasmid constructs encoding the two domains of IL-12 (MFGS-IL12) or one plasmid containing a fusion gene, Flexi-12 under a CMV promoter.

Figure 8:
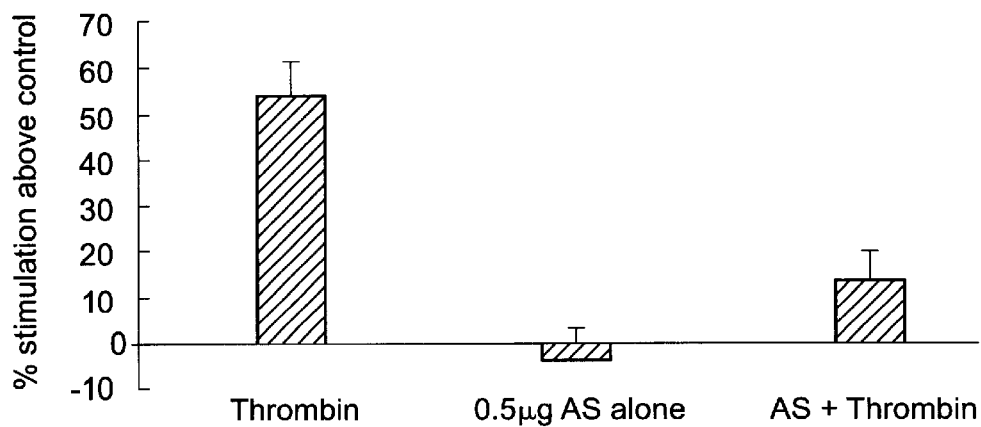

FIG. 8 shows the effect of transfection with anti-sense oligonucleotides (AS) to the thrombin receptor (PAR-1) on thrombin induced proliferation of human foetal lung fibroblasts (HFL-1 cells).

Figure 9:
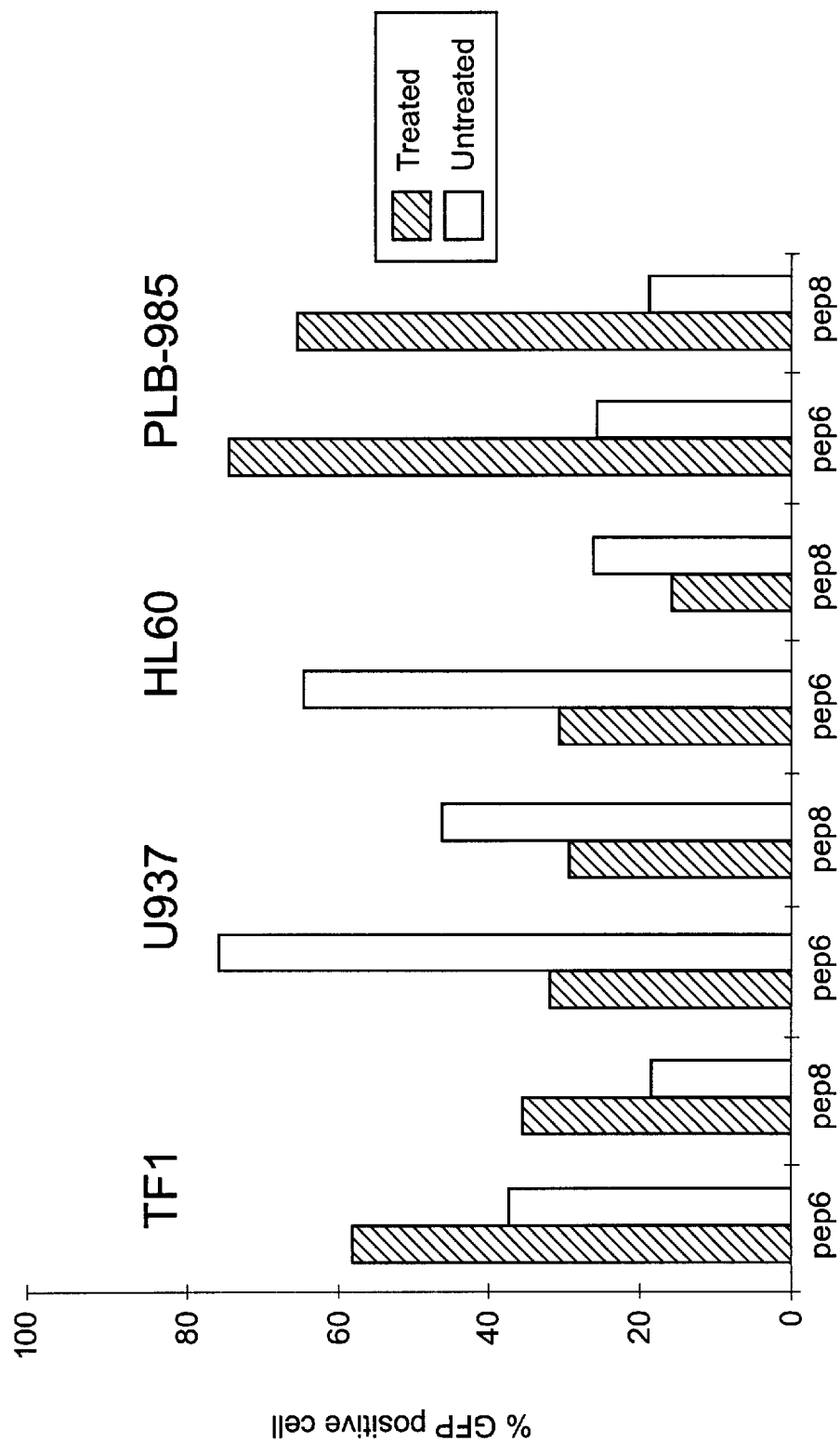

FIG. 9 shows the effect of transfection of haematopoietic cell lines HL60, PLB985, TF1 and U937 with LID complexes containing lipofectin, the reporter gene pEGFP-N1 and either $[K]_{16}$-peptide 6 (pep 6) or $[K]_{16}$-peptide 8 (GGCRGDMFGCA [SEQ.ID.NO.:8] pep 8) compared with untreated cells. The percentage of GFP positive cells is determined using a fluorescence activated cell sorter.

EXAMPLES

Materials & Methods

Cell Lines

The cell line COS-7 (monkey kidney epithelial cells) were maintained in Dulbecco's Modified Eagle Medium (DMEM; Life Technologies, Paisley, U.K.) supplemented with 10% foetal calf serum (FCS), L-glutamine, penicillin and streptomycin. ECV304 (spontaneously transformed human umbilical vein endothelial cells) were grown in 199 Medium (Life Technologies, Paisley, U.K.). HT1080 fibrosarcoma cells and A375M melanoma cells were maintained in DMEM and 10% FCS. IMR2 neuroblastoma cells were grown in DMEM F12 Nutrient Mix (Life technologies). Cell lines were all grown in a 37° C. incubator with a 5% $CO_2$ water-saturated atmosphere.

Peptide synthesis

The sequence of peptide 6, GACRRETAWACG, was based on an α5β1-specific peptide from a phage display library (Koivunen et al., 1995). The oligolysine-peptide $[K]_{16}$GACRRETAWACG was synthesised as follows:

Protected amino acids and preloaded Gly-Wang resin were obtained from Calbiochem-Novabiochem (Nottingham, U.K.). Solvents and HBTU [2-(1H-benzotriazol-1-yl)-1,1,3,3-tetram-ethyluronium hexafluorophosphate] were obtained from Perkin-Elmer Applied Biosystems, U.K. The peptide was synthesised on a Model 431A updated Applied Biosystems Solid Phase Synthesiser on 0.1 mmol preloaded Gly-Wang resin (Calbiochem-Novabiochem, Nottingham, U.K.) using basic feedback monitoring cycles and HBTU as a coupling reagent. 9-fluorenylmethyloxy-carbonyl was used for temporary α-amino group protection. Side-chain protecting groups were tert-butyloxycarbonyl for Lys and Trp, trityl for Cys, 2,2,5,7,8-pentamethylchroman-6sulphonyl for Arg, tert-butylester for Glu and tert-butyl ether for Thr. Cleavage from the resin and deprotection of the peptide was achieved by treating the peptidyl-resin with 10 ml of a mixture containing 10 ml trifluoroacetic acid, 0.25 ml ethanedithiol, 0.25 ml triisopropylsilane at 20° C. for two hours. The peptide was precipitated using ice-cold diethylether and then filtered through a fine sintered glass filter funnel under light vacuum. The peptide precipitate was dissolved in 10% acetic acid/water solution and freeze dried. The crude peptide was analysed by reverse phase HPLC and matrix assisted laser desorption ionisation time of flight mass spectroscopy. Purity of the crude peptide was about 70% by reverse phase HPLC, and mass analysis using a Finnegan LazerMat gave a molecular weight of 3331.5 for the MH+ ion which was in excellent agreement with calculated weight for MH+ ion of 3331.46.

Oligolysine-peptide 1: $[K]_{16}$GACRGDMFGCA and oligolysine-peptide 5: $[K]_{16}$GACDCRGDCFCA were obtained from Zinsser Analytic (Maidenhead, U.K.).

Plasmid DNA

The plasmids pGL2, which contains a luciferase reporter gene (Promega, Madison, Wis., U.S.A.) and pCMVβ, which contains a β-galactosidase reporter gene (Clontech, Palo Alto, Calif., U.S.A.) were grown in Escherichia coli DH5a and purified, after bacterial alkaline lysis, on Qiagen resin columns (Qiagen Ltd., Crawley, U.K.) by the manufacturer's instructions. Isopropanol-precipitated DNA pellets were washed with 70% ethanol then dissolved in water or TE buffer (10 mM Tris-Cl, pH 8.0 and 1 mM EDTA).

Spectrophotometric measurements of plasmid solutions were used to assess plasmid concentration ($A_{260}$) and purity ($A_{260}/A_{280}$ ratio). Plasmid solutions were adjusted to a concentration of 1 mg/ml and stored at 4° C.

Formation of Transfection Complexes

Cells were seeded into 24-well plates at $5 \times 10^4$ cells per well then incubated overnight at 37° C. in complete growth medium. The following day, transfection complexes were made from the following stock solutions, all prepared in OptiMEM (Life Technologies, Paisley, U. K.), lipofectin (an equimolar mixture of the cationic lipid N-[1-(2,3-dioleyloxy)propyl]-N,N,N-trimethylammonium chloride (DOTMA) and the neutral lipid dioleoyl phosphatidylethanolamine (DOPE), obtained as "Lipofectin" from Life Technologies, Paisley, U.K.) (1 mg /ml), pGL2-control (1 mg/100 ml) and $[K]_{16}$/integrin-targeting peptide 1, 5 or 6 (0.1 mg/ml).

Complexes were made usually with three components: oligolysine-peptide (I), plasmid DNA or RNA (D) and lipofectin (L), by mixing together the different components with an automatic pipette. The mixture LID was made in the same way in the optimal weight ratio 0.75:4:1 (L:I:D). Both types of mixture were left to aggregate for at least 30 min then diluted to a concentration of one microgram DNA per 0.5 ml with OptiMEM. The growth medium was removed from each well then 0.5 ml of transfection complex added. The plate was then returned to the incubator for four to six hours. The transfection medium was then removed and replaced with 1 ml of complete growth medium. Transfected cells were incubated for 48 to 72 hours then assayed for reporter gene activity.

Luciferase Assays

Cells transformed with pGL2 were washed twice with PBS to remove serum then 100 microlitres of Reporter Lysis Buffer (Promega, Madison, Wis., U.S.A.) was added to each well and placed at 40° C. for 15 to 30 minutes. Cells were then dislodged by scraping with a yellow micropipette tip. Cellfree lysates were then prepared and assayed with a Luciferase Assay kit (Promega, Madison, Wis., U.S.A.) following the manufacturer's instructions. Total light emission was measured for 60 seconds on an LKB 1251 Luminometer (Labtech, Uckfield, U.K.). The protein concentration of each sample was then determined with Protein Assay Reagent (BioRad, Hercules, Calif., U.S.A.) and luciferase enzyme activity expressed in terms of relative light units per milligram of protein (RLU/mg).

LacZ Assays β-galactosidase activity was detected by staining with X-gal. After washing with PBS cells were fixed to the plastic plates by addition of 0.5% glutaraldehyde in PBS for 20 minutes at 40° C. Wells were washed with PBS and cells were stained with X-gal at 370° C. for up to six hours.

Atomic Forces Microscopy (AFM)

Atomic forces microscope analysis of transfection complexes was performed as described previously (Wolfert & Seymour, 1996) using an AFM-2, part of the NanoScope II (Digital Instruments, Santa, Barbara, U.S.A.). Transfection complexes of $[K]_{16}$-peptide 6/pGL2, with and without lipofectin, were prepared as described above except that water was used as the diluent for all components rather than OptiMEM.

Example 1

Effect of Different Amounts of Lipofectin (DOTHA/DOPE) on Transfection

Figure 1:
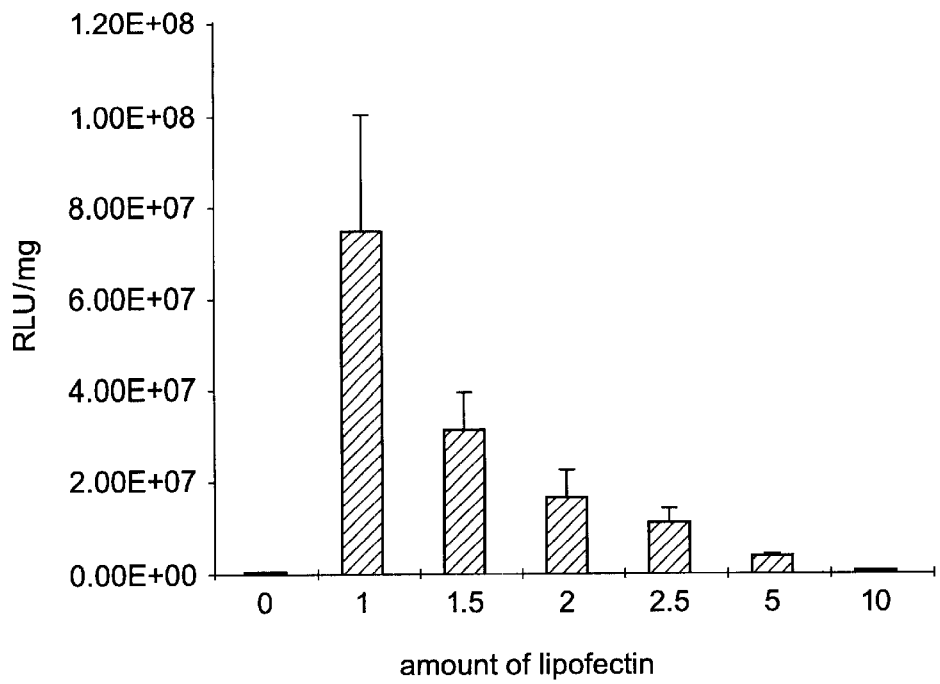
FIG. 1 shows the effect of different amounts of lipofectin (DOTMA:DOPE) on the enhancement of transfection of ECV304 cells using a complex consisting of lipofectin, oligolysine-peptide 1 ($[K]_{16}$GACRGDMFGCA [SEQ.ID.NO.:19]) and plasmid pGL2.

Transfection complexes were prepared as described above in the Materials & Methods section. The complexes were made by mixing solutions of oligolysine-peptide 1 ([K]$_{16}$GACRGDMFGCA) at 0.1 mg/ml in OptiMEM low serum tissue culture medium with a solution of lipofectin (DOTMA/DOPE cationic liposome as above) in a range of concentrations from 1 to 10 μg/100 μl in optiMEM. Finally, the appropriate amount of pGL2-control plasmid DNA (0.1 mg/ml) was added and mixed by repeated pipetting. The ratio of mixing of each component was a constant 4 μg of oligolysine-peptide per μg of DNA, while the proportion of lipofectin varied from 1 to 10 μg per μg of DNA. ECV304 cells were transfected with the complexes as described above, incubated for 48 hours then assayed for luciferase expression as described above. The results are shown in FIG. 1.

Complexes formed with 1 μg of lipofectin and 4 μg of oligolysine-peptide per microgram of plasmid were almost 100-fold ore active than complexes lacking lipofectin. Addition of larger amounts of lipofectin reduced transfection activity in a lipofectin dose-dependent manner.

Similar results were obtained with $[K]_{16}$-peptide 6.

Example 2

Effect of Different Amounts of Lipofectin on Transformation in Three Different Cell Lines Experiments were then performed to refine the optimal amount of lipofectin in LID transfection complexes using three different cell lines A375M (melanoma cells), COS-7 (monkey kidney epithelial cells) and ECV304 (human umbilical cord endothelial cells).

Transfection complexes were made as described in Example 1 but using a narrower range of amounts of lipofectin. Lipofectin/-oligolysine-peptide/DNA complexes were prepared with constant amounts of $[K]_{16}$-peptide 1 ([K]$_{16}$GACRGDMFGCA) (4 μg) and pGL2 (1 μg) plasmid DNA and a range of lipofectin amounts (1 to 2.5 micrograms). Complexes were used to transfect A375M, COS-7 and ECV304 cells, which were then harvested two days later for luciferase expression analysis.

Figure 2:
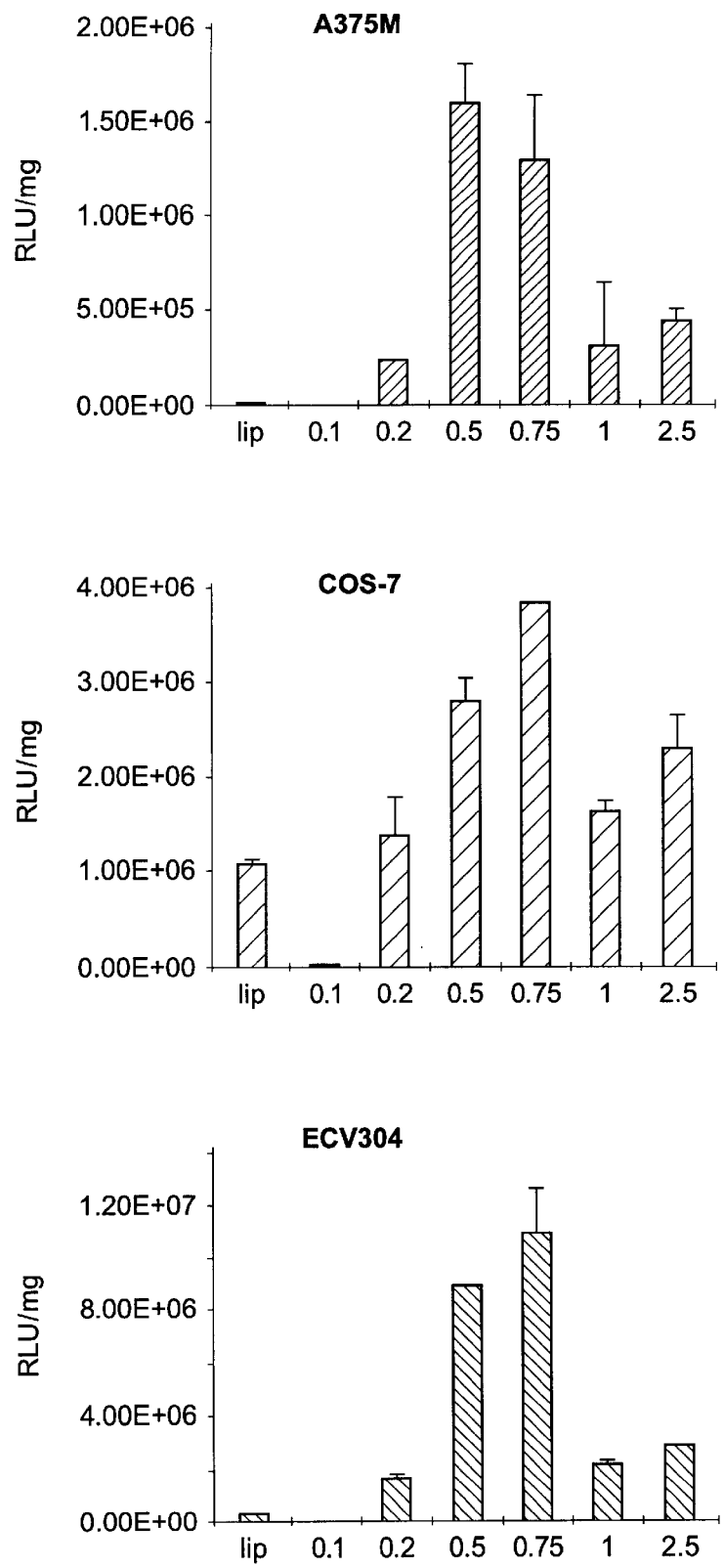
FIG. 2 shows the effect of different amounts of lipofectin on the enhancement of transfection of A375M, COS-7 and ECV-40 cells using a complex consisting of lipofectin, oligolysine-peptide 1 ($[K]_{16}$GACRGDMFGCA) and plasmid pGL2.

The results are shown in FIG. 2. In each case the optimal transfection ratio peaked at 0.75 μg of lipofectin per microgram of plasmid DNA. This combination of the amounts of the components was maintained in all subsequent examples.

A mixing ratio L:I:D of 0.75:4:1 by weight corresponds to a molar ratio of 0.5 nmol lipofectin: 1.25 nmol oligolysine-peptide 1: 0.25 pmol pGL2-control. The molar charge of each component is 0.5 moles positive charge per mole lipofectin, seventeen moles positive charge,per mole $[K]_{16}$-peptide 1 and 12,000 moles negative charge per mole of pGL2 (6 kb). Therefore, in the optimal transfection complex, 3 nmol of negative charge from the plasmid is mixed with 21 nmol of positive charge from oligolysine-peptide 1 and 0.25 nmol positive charge from lipofectin. Hence the charge ratio of approximately 7:1 positive to negative charges in ID complexes is little altered by the incorporation of 0.25 nmol positive charge from lipofectin into high efficiency LID transfection complexes. It is likely, therefore, that the improvement in transfection efficiency of LID complexes is not charge related.

Example 3

Effect of the Order in Which the Components of the Complex are Mixed.

To determine the procedure for the production of optimal LID transfection complexes transfections were performed with complexes made by adding the components of the complexes in different orders. All combinations were prepared with the same amounts and concentrations of the components (1 μg pGL2 plasmid DNA, 0.75 μg of lipofectin and 4 μg of oligolysine-peptide 1 ([K]$_{16}$GACRGDMFGCA). Transfections were performed in ECV304 cells and luciferase activity was assessed as described above.

Figure 3:
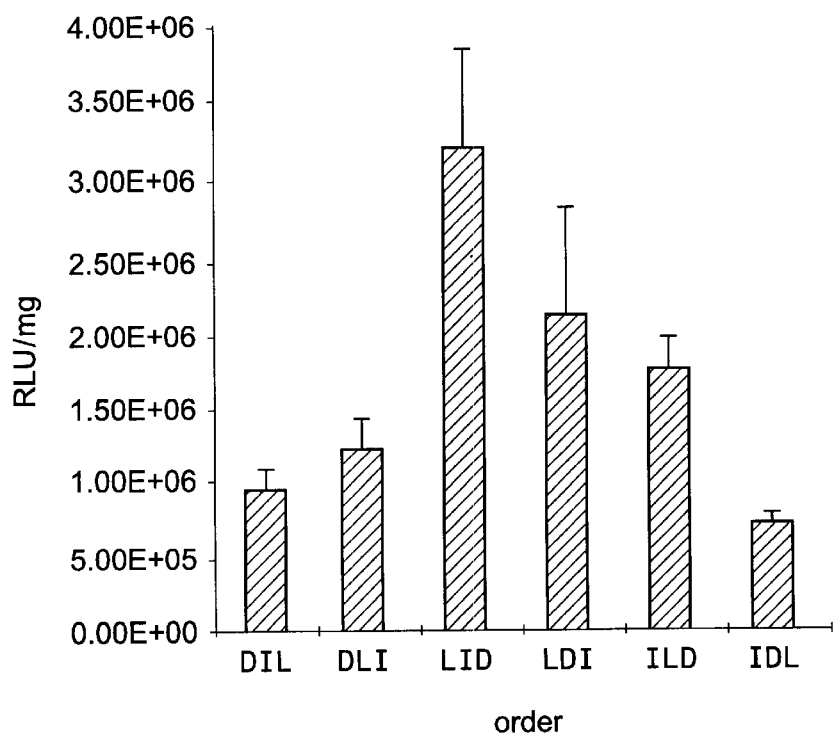
FIG. 3 shows the effect of the order of mixing the components of a complex consisting of lipofectin (L), oligolysine-peptide 1 ($[K]_{16}$GACRGDMFGCA) (I) and plasmid pGL2 (D) on the enhancement of transfection of ECV40 cells.

The results are shown in FIG. 3 in which D represents the plasmid vector pGL2, I represents $[K]_{16}$-peptide 1 and L represents lipofectin. The expression data indicates that the order of mixing LID was optimal. Significantly, combinations in which the lipofectin was the last component added were least efficient. The order of mixing, LID, was employed in all subsequent transfection experiments.

Example 4

Transfection Rates

Cells were transfected with optimised oligolysine-peptide/lipofectin/pCMVβ complexes as described in Examples 1 and 2 prepared in the order of mixing LID but using pCMVB as the plasmid vector (component D) instead of pGL2. The cells were stained for β-galactosidase activity with X-gal as described above. A number of cell types, A375M, COS7 and ECV304 displayed transfection efficiencies of 50 to 100% compared to 1 to 10% achieved with oligolysine-peptide/DNA complexes alone. This represents a very significant improvement in transfection efficiency.

Example 5
Comparison of Enhancement with Lipofectin and with Different Oligolysine-peptides To compare the effect of different integrin-targeting oligolysine-peptides, duplicate sets of complexes were formed with plasmid pGL2 and one of the following:

oligolysine-peptide 1 ([K]$_{16}$GACRGDMFGCA, pep 1),
oligolysine-peptide 5 ([K]$_{16}$GACDCRGDCFCA, pep 5),
oligolysine-peptide 6 ([K]$_{16}$GACRRETAWACG, pep 6), and [K]$_{16}$.

One set of complexes also contained lipofectin (lip), the other was without lipofectin. A control complex containing plasmid pGL2 with lipofectin and [K]$_{16}$lysine-peptide 1 in a ratio by weight of 4:1 was prepared.

Each complex was used to transfect cell lines and luciferase expression determined. Complexes were made with (lip) and without lipofectin. An optimised complex was performed for comparison. All oligolysine-peptides were mixed with lipofectin and plasmid DNA (KLD) in the same optimised charge ratios and order of mixing.

The results are shown in FIG. 4. Although KLD complexes were usually better transfection agents than KD or LD complexes, LID complexes generated luciferase expression levels three to six-fold higher than KLD complexes. Expression levels from LID complexes containing oligolysine-peptide 5 were two-fold lower than those containing oligolysine-peptide 1 or oligolysine-peptide 6, which may reflect the differing integrin receptor affinities of the peptides. The transfection enhancement of the LID complexes was observed with all the peptides tested, two of which (peptides 1 and 5) contain the conserved RGD sequence, one of which (peptide 6) does not.

Example 6
Specificity

To demonstrate integrin specificity, LID complexes were prepared with constant amounts of plasmid pGL2-control and lipofectin, and a range of combinations of [K]$_{16}$-peptide 6 and [K]$_{16}$. A total of 40 µg of [K]$_{16}$-peptide was used, consisting of 30 1, 5, 10, 20, 35, 39 µg of [K]$_{16}$-peptide 6 made up to 40 µg with [K]$_{16}$.

Transfections were performed as described in Example 1 and luciferase assays performed after 48 hours. The results are shown in FIG. 5. Transfection efficiency demonstrated an apparently exponential increase with increasing amounts of oligolysine-peptide 6, and, therefore, a dose-dependent response to the amount of available integrin-binding ligands. Accordingly, while both the sixteen-lysine domain, and the lipofectin components are themselves capable of mediating transfection, both individually and in [K]$_{16}$/lipofectin combination complexes, the highest efficiency transfection is directly proportional to the amount of available integrin-binding ligand.

Example 7
Atomic Force Microscopy

Atomic force microscopy experiments were performed to determine and compare the structures formed by mixing 4 µg [K]$_{16}$peptide 6 and 1 µg pGL2-control plasmid DNA (ID complexes). LID complexes were formed from [K]$_{16}$-peptide 6 (4 µg)/lipofectin (0.75 µg)/DNA (1 µg) in the order LID which was shown to yield optimal transfection results. Lipofectin/DNA complexes (LD) were formed at two different ratios; an optimal transfection ratio of 5 µg lipofectin per microgram of pGL2 and the same ratio as used in LID complexes, 0.75 µg lipofectin per microgram of plasmid.

The results are shown in FIG. 6. ID complexes, composed of oligolysine-peptide 6 and plasmid DNA, were examined initially by AFM within fifteen minutes of mixing the two components. The complexes formed particles of low polydispersity which, on the mica coverslips, had a diameter of approximately 200 nm. A computer-generated contour map revealed that the particles formed were of irregular conical shape. LID complexes assessed by AFM formed particles of a similar size and shape to ID complexes. The additional lipofectin did not, apparently, disrupt the particles. LD complexes, however, formed at the 5:1 ratio appeared as a network of tubes with occasional particles associated with the tubes. LD complexes formed at the lower ratio (0.75:1), however, appeared to be short tubular structures. LD complexes formed at this lower ratio were inactive in transfection experiments. LID complexes formed as above were also analysed by AFM after standing overnight. Particles were now smaller in size with diameters of approximately 50–100 nm suggesting that the particles had compacted. Computer-generated computer maps represented these particles as regular conical structures. The cones were measured and their volumes were calculated. The spheres which the particles are predicted to form when free in solution were then calculated to be 20 to 60 nm in diameter. In transfection experiments with pGL2 the compact particles formed overnight in water yielded luciferase expression results approximately twice as high as the freshly made complexes.

Example 8
Transfection of Neuroblastoma Cells

Transfection of three different human neuroblastoma cell lines, SHSY-5Y, KELLY and IMR-32 and one mouse neuroblastoma cell line, Nb2A, was optimised using an LID complex containing [K]$_{16}$-peptide 6, lipofectin and either luciferase or GFP as reporter gene, as described in the Materials and Methods section and the Examples above.

The three human neuroblastoma cell lines and COS-7 cells were then transfected using the same LID complex with, instead of the reporter gene, one of two different IL-12 expressing vectors. One vector expresses a fusion protein of the two chains of IL-12, p35 and p40, (Flexi-12; Anderson et al. 1997) This fusion is regulated by a CMV promoter. The second IL-12 expression system consists of two retroviral constructs MFGS-p35 and MFGS-p40, which are retroviral plasmid constructs encoding the two separate chains of interleukin-12 (IL-12). Both genes are regulated by the retroviral long terminal repeats (LTRs). The vectors were obtained from Professor Mary Collins, UCL, London.

Secreted IL-12 expression was monitored by ELISA 48 hours after transfection. The transfected cells were found to secrete high levels of the cytokine, see FIG. 3. The Flexi-12 construct was most efficient.

These results demonstrate that the transfection system of the present invention is suitable for use in a vaccine for neuroblastoma, an important childhood malignancy, and also for vaccines against other cancers.

Example 9
Transfection of Lung bronchial Epithelium in Vivo

LID complexes comprising [K]$_{16}$-peptide 6 and lipofectin in the optimal ratio L:I:D of 0.75:4:1 mixed in the order LID were made as described in the Materials and Methods section above but using a solution of the oligolysine-peptide in phosphate buffered saline (PBS) at a concentration of 1 mg/ml. The other components were in solution in water, lipofectin at a concentration of 1 mg/ml and DNA encoding a nuclear localising beta-galactosidase reporter gene pAB11 at a concentration of 1 mg/ml. The oligolysine-peptide was used at high concentration to minimise the final volume of the complex, and PBS was used instead of OptiMEM for bio-compatibility.

Lewis rats were anaesthetized and then injected through the trachea into the airway with 287.5 μl of complex comprising 37.5 1 lipofectin, 200 μg [K]$_{16}$-peptide 6 in 200 μl PBS, and 50 μg pAB11 in 50 μl water. The animals were sacrificed at 24 hours, the lungs removed, fixed and stained with X-gal, then sectioned and examined. Extensive staining was seen in the bronchial epithelium in the upper airway.

This result demonstrates the utility of the transfection complex of the present invention for gene therapy of disease involving the lungs and airways, for example, cystic fibrosis and asthma.

Example 10
Transfection of Corneal Endothelium in Vivo

LID complexes were made as described in Example 10 for in vivo lung transfections. The LID complex-containing solution was injected into the anterior chamber of the eye of mice. The volume of solution injected in each case was 2 μl, thus delivering approximately 0.2 μg of pAB11 plasmid DNA. Efficient gene transfer to the corneal endothelium was demonstrated by X-gal staining.

The high transfection rate demonstrates the utility of the transfection complex of the invention of the treatment of eye diseases affecting the cornea, and for corneal transplantation.

Example 11
Transfections of Primary Smooth Muscle cells and Cardiac Myocytes Tissue cultures of rat primary smooth muscle cells (aortic smooth muscle cells) and cardiac myocytes were prepared according to standard methods (Blank et al. 1988). An LID complex comprising lipofectin, [K]$_{16}$-peptide 6 and GFP as a reporter gene in the optimal LID ratio and mixing order was prepared as described in the Materials and Methods section and the Examples above. The tissue cultures were transfected with the LID complex as described in the Material and Methods section above. Fluorescing imaging of GFP-expressing cells demonstrates transfection efficiency in excess of 50%.

Primary smooth muscle cells and cardiac myocytes are particularly resistant to plasmid-mediated transfection using most other non-viral vectors. In contrast, the transfection complex of the present invention achieved transfection efficiencies in excess of 50%, thus demonstrating the utility of the complexes for treatment of diseases affecting muscle, including smooth muscle and cardiac muscle.

Example 12
Transfections with High Molecular Weight Constructs

Different size constructs can be delivered with the transfection complex of the present invention. A fibroblast culture was transfected as described in the Materials and Methods section with an LID complex comprising [K]$_{16}$-peptide 6, lipofectin and a 130 kB DNA construct. The complex, comprising the LID components in the optimal ratio and mixing order, was prepared as described in the Methods and Materials section and Examples above. Transfection was achieved with 2–3% efficiency.

Cellular process associated with the enhanced integrin-mediated internalisation of DNA using a complex of the present invention are more closely related to phagocytosis than endocytosis and are thus particularly suited to the delivery of complexes containing very large DNA molecules.

Example 13
Transfection with Anti-sense DNA

Thrombin stimulates proliferation of human lung fibroblasts. Thrombin-treated human lung fibroblasts (HFL-1 cells) proliferated 53% in response to thrombin. 24 hours before treatment with thrombin, HFL-1 cells were treated with an LID complex comprising [K]$_{16}$-peptide 6, lipofectin and a 20-mer antisense oligonucleotide directed against the thrombin receptor PAR-1 in the optimal ratio and mixing order prepared as described in the Materials and Methods section and the Examples above. The antisense oligonucleotide-containing complex was in contact with the cells for 4 hours. 24 hours after the start of the treatment with the complex, treatment with thrombin was carried out.

The thrombin-induced proliferation was attenuated by 76% +/−12% by the pre-treatment with the LID complex. Cells treated with the antisense-containing complex but not with thrombin did not proliferate.

This result demonstrates the utility of the complex of the invention for efficient intracellular transport of antisense oligonucleotides, as is required for antisense therapy, for example, antiviral and anticancer therapy.

Example 14
Transfection of Haematopoietic Cells

Haematopoietic cells are particularly resistant to transfection with most plasmid-mediated vectors.

LID complexes were prepared as described in the Material and Methods section and Examples above using lipofectin and [K]$_{16}$-peptide 6, which targets α5β11 integrins, and pEGFP-N1 (Promega) as reporter gene. Complexes were prepared analogously substituting [K]$_{16}$-peptide 8 ([K]$_{16}$GACQIDSPCA SEQ.ID.NO.:21), which targets α4β1 integrins, for [K]$_{16}$-peptide 6. The complexes were prepared by mixing the components in the optimal ratio and mixing order as described in the Materials and Methods section and Examples above.

Four different haematopoietic cells lines (HL60, PLB985, TF1 and U937) were transfected as described in the Materials and Methods section with the following modifications: cells were untreated or were treated with Gm-CSF (10ng/ml) for TF1 cells or phorbol myristic acid (PMA) for the other three cells lines prior to transfection. Transfection with the LID complexes containing pEGFP-N1 generated a transfection efficiency of more than 60% in all four lines as measured on fluorescent activated cell sorter, see FIG. 8.

These results demonstrate the utility of the transfection complex of the invention for gene therapy involving haematopoietic cells, for example, gene therapy of leukaemia and bone marrow stem cell disorders. This is particularly useful because, as pointed out above, haematopoietic cells are particularly resistant to transfection with most plasmid-mediated vectors.

REFERENCES

1. Wu GY, Wu CH. Receptor-mediated in vitro gene transformation by a soluble DNA carrier system. J Biological Chemistry 1987;262(10):4429–4432.
2. Wagner E, Cotten M, Mechtler K, Kirlappos H, Birnstiel M L. DNA-binding transferrin conjugates as functional gene-delivery agents: Synthesis by linkage of polylysine or ethidium bromide to the transferrin carbohydrate moiety. Bioconjugate Chemistry 1991;2:226–231.

3. Cotten M, Lange. Transferrin-polycation-mediated introduction of DNA into human leukemic cells: Stimulation by agents that affect the survival of transfected DNA or modulate transferrin receptor levels. PNAS 1990;87:4033–4037.
4. Ferkol T, Perales J C, Eckman E, Kaetzel C S, Hanson R W, Davis P B. Gene transfer into the airway epithelium of animals by targeting the polymeric immunoglobulin receptor. J Clinical Investigation 1995;95:493–502.
5. Curiel D T, Agarwal S, Wagner E, Cotten M. Adenovirus enhancement of transferrin-polylysine-mediated gene delivery. PNAS 1991;88:8850–8854.
6. Fernandez M A, Muno-Fernandez M A, Fresno M. Involvement of β1 integrins in the binding and entry of *Trypanosoma cruzi* into human macrophages. European J of Immunology 1993;23:552–557.
7. Wickham T J, Filardo E J, Cheresh D A, Nemerow G R. Integrin αvβ5 selectively promotes adenovirus mediated cell membrane permeabilization. J Cell Biology 1994;127 (1):257–264.
8. Bergelson J M, Shepley M P, Chan B M C, Hemler M E, Finberg R W. identification of the integrin VLA-2 as a receptor for echovirus 1. Science 1992;255:1718–1720.
9. Logan D, Abu-Ghazaleh R, Blakemore W, et al. Structure of a major immunogenic site on foot-and-mouth disease virus. Nature 1993;362:566–568.
10. Isberg R R. Discrimination between intracellular uptake and surface adhesion of bacterial pathogens. Science 1991;252:934–938.
11. Almeida E A C, Huovilla A-P J, Sutherland A E, et al. Mouse 25 egg integrin α6β1 functions as a sperm receptor. Cell 1995;81:1095–1104.
12. Clements J M, Newham P, shepherd M, et al. Identification of a key integrin-binding sequence in VCAM-1 homologous to the LDV active site in fibronectin. J Cell Science 1994;107:2127–2135.
13. Lu X, Deadman J J, Williams J A, Kakkar V V, Rahman S. Synthetic RGD peptides derived from the adhesive domains of snake-venom proteins: evaluation as inhibitors of platelet aggregation. Biochemistry J 1993;296:21–24.
14. Koivunen E, Wang B, Ruoslahti E. Phage libraries displaying cyclic peptides with different ring sizes: ligand specificities of the RGD-directed integrins. Biol/Technology 1995;13:265–270.
15. Koivunen E, Gay D A, Ruoslahti E. Selection of peptides binding to the α5β1 integrin from phage display library. J Biological Chemistry 1993;268(27):20205–20210.
16. Koivunen E, Wang B, Ruoslahti E. Isolation of a highly specific ligand for the α5β1 integrin from a phage display library. J Cell Biology 1994;124(3):373–380.
17. O'Neil K T, Hoess R H, Jackson A, Ramachandran N S, Mousa A, DeGrado W F. Identification of novel peptide antagonists for GPIIb/IIIa from a conformationally constrained phage peptide library. Proteins 1992;14:509–515.
18. Healy J M, Murayama O, Maeda T, Yoshino K, Sekiguchi K, Kikuchi M. Peptide ligands for integrin alpha v beta 3 selected from random phage display libraries. Biochemistry 1995;34:3948–3955.
19. Pasqualani R, Koivunen E, Ruoslahti E. A peptide isolated from phage display libraries is a structural and functional mimic of an RGD-binding site on integrins. J Cell Biology 1995;130:1189–1196.
20. Hart S L, Knight A M, Harbottle R P, et al. Cell binding and internalization by filamentous phage displaying a cyclic Arg-Gly-Asp-containing peptide. J Biological Chemistry 1994;269:12468–12474.
21. Hart S L, Harbottle R P, Cooper R, Miller A, Williamson R, Coutelle C. Gene delivery and expression mediated by an integrin-binding peptide. Gen Therapy 1995;2:552–554.
22. Wolfert M A, Seymour L W. Atomic force microscopic analysis of the influence of the molecular weight of poly(L)lysine on the size of polyelectrolyte complexes formed with DNA. Gene Therapy 1996;3:269–273.
23. Hart S L, Collins L, Gustaffson K, Fabre J W. Integrin mediated transfection with peptides containing arginine-glycine-aspartic acid domains. In press 1997.
24. Farhood H, Sebina A, Huang L. The role of dioleyl phos-phatidylethanolamine (DOPE) in cationic liposome mediated gene transfer. Biochem Biophys Acta 1995;1235:289–295.
25. Anderson R, MacDonald I, Corbett T, Hacking G, Lowdell M W and Prentice H G. Human Gene Therapy 1997;8:1125–1135.
26. Blank R S, Thompson M M and Owens G K. Journal of Cell Biology 1988;107:299.

What is claimed is:

1. A transfection comprising a first component comprising one or more lipids, a second component comprising an oligolysine linked via a peptide bond to an integrin-binding peptide, and a third component comprising a nucleic acid, said complex being produced by a process comprising mixing said first component with second component prior to addition of said third component.

2. A complex as claimed in claim 1, wherein the integrin-binding peptide comprises the conserved amino acid sequence arginine-glycine-aspartic acid (RGD).

3. A complex as claimed in claim 2, wherein the peptide has at least two cysteine residues that form at least one disulphide bond to form a cyclic peptide wherein said peptide comprises an RGD sequence between said at least two cysteine residues.

4. A complex as claimed in claim 3, wherein the peptide comprises the sequence CRGDMFGC (SEQ ID NO: 5).

5. A complex as claimed in claim 3, wherein the peptide comprises the sequence GGCRGDMFGC (SEQ ID NO: 6), GGCRGDMFGCG (SEQ ID NO: 7), GGCRGDMFGCA (SEQ ID NO: 8) or GACRGDMFGCA (SEQ ID NO: 9).

6. A complex as claimed in claim 3, wherein the peptide comprises the sequence GACDCRGDCFCA (SEQ ID NO: 10).

7. A complex as claimed in claim 1, wherein the peptide comprises the sequence CRRETAWAC (SEQ ID NO: 13).

8. A complex as claimed in claim 7, wherein the peptide comprises the sequence GACRRETAWACA (SEQ ID NO: 11) or GACRRETAWACG (SEQ ID NO: 12).

9. A complex as claimed in claim 1, wherein the peptide comprises the sequence GAGPEILDVPST (SEQ ID NO: 14), GACQIDSPCA (SEQ ID NO: 15) or GACRRETAWACGKGACRRETAWACG (SEQ ID NO: 16).

10. The complex of claim 1, wherein the nucleic acid of the third component comprises a transcriptional control element and, optionally a translational control element.

11. A complex as claimed in claim 1, wherein the nucleic acid of the second component is DNA.

12. A complex as claimed in claim 1, wherein the nucleic acid of the second component is RNA.

13. A complex as claimed in claim 1, wherein the oligolysine has from 10 to 20 lysine residues.

14. The complex of claim 1, wherein the first component comprises a cationic lipid and a neutral lipid having a membrane destabilising or fusogenic property.

15. The complex of claim 14, wherein the first component comprises the neutral lipid dioleyl phosphatidylethanolamine (DOPE).

16. The complex of claim 1, wherein the first component comprises the cationic lipid N-[1-(2,3-dioleyloxy)propyl]-N,N,N-trimethylammonium chloride (DOTMA).

17. The complex of claim 1, wherein the first component comprises a mixture of DOPE and DOTMA.

18. A complex as claimed in claim 17, wherein the first component comprises an equimolar mixture of DOPE and DOTMA.

19. The complex of claim 1, which comprises an equimolar mixture of DOPE and DOTMA as the lipid component and $[K]_{16}$ as the oligolysine of said second component.

20. The complex of claim 1 which comprises an equimolar mixture of DOPE and DOTMA as the lipid component and $[K]_{16}$ as the oligolysine of said second component, said first, second and third components and second component being present in a ratio of 0.75:4:1 by weight or 0.5 nmol:1.25 nmol:0.25 nmol on a molar basis.

21. The complex of claim 1, wherein the first component comprises 2,3-dioleyloxy-N-[2-(spermidinecarboxamido)ethyl]-N,N-dimethyl-1-propanaminium-trifluoridoacetate (DOSPA).

22. The complex of claim 1, wherein the first component comprises a mixture of DOPE and DOSPA.

23. The complex of claim 1, which comprises a mixture of DOPE and DOSPA as the first component and $[K]_{16}$ as the oligolysine of said second component.

24. The complex the claim 1 which comprises a mixture of DOPE and DOSPA as the lipid component and $[K]_{16}$ as the oligolysine of said second component, wherein said first, second, and third components are present in a ratio of 12:4:1 by weight.

25. A process for producing the complex of claim 1, which comprises mixing components in the following order: first component, second component, and third component.

26. A mixture obtained by mixing a first component consisting essentially of one or more lipids and a second component consisting of an oligolysine linked via a peptide bond to an integrin-binding peptide.

27. The mixture of claim 26, which comprises an equimolar mixture of DOPE and DOTMA as the first component and $[K]_{16}$ as the oligolysine of said second.

28. The mixture of claim 27, wherein said first component and said second component are present in a ratio of 0.75:4 by weight.

29. A process for producing the complex of claimed in claim 1, comprising mixing the third component with the mixture of claim 26.

30. A method of transfecting a cell with a nucleic acid, which comprises introducing into the cell in vitro or the complex of claim 1.

31. A kit that comprises the mixture of claim 26 or, individually, said first component and said second component.

32. The kit claim 31, comprising a plasmid, vector or nucleic acid.

33. A method for expressing a nucleic acid in a host cell, which comprises, introducing into the cell in vitro the complex of claim 10, such that said nucleic acid is expressed in said host cell.

34. A method for producing a protein, comprising:

(a) transfecting a cell in vitro with the complex of claim 10, wherein the nucleic acid of the third component encodes said protein;

(b) culturing said cell under conditions suitable for expression of said protein; and (c) recovering said protein from said cultured cell.

* * * * *